(12) United States Patent
Boyce et al.

(10) Patent No.: US 6,815,214 B2
(45) Date of Patent: Nov. 9, 2004

(54) PHARMACEUTICAL USES AND SYNTHESIS OF DIKETOPIPERAZINES

(75) Inventors: Jim P. Boyce, Kirkland, WA (US); J. Jeffry Howbert, Bellevue, WA (US); John C. Tabone, Bothell, WA (US)

(73) Assignee: Celltech R & D, Inc., Slough (GB)

(*) Notice: Subject to any disclaimer, the term of this patent is extended or adjusted under 35 U.S.C. 154(b) by 119 days.

(21) Appl. No.: 10/035,594

(22) Filed: Dec. 28, 2001

(65) Prior Publication Data

US 2002/0187984 A1 Dec. 12, 2002

Related U.S. Application Data

(60) Provisional application No. 60/259,359, filed on Dec. 29, 2000.

(51) Int. Cl.[7] ............ G01N 24/00; G01N 33/534; A61K 31/498; C07D 401/02
(52) U.S. Cl. .......... 436/173; 435/8; 435/7.21; 436/57; 436/98; 436/501; 436/503; 436/504; 436/804; 436/815; 514/249; 514/252.12; 544/349; 544/360; 544/362; 544/364; 544/366; 544/367; 544/383
(58) Field of Search .................. 436/173, 57, 98, 436/501, 503, 504, 804, 815; 435/8, 7.21; 514/249, 252.12, 349, 360, 362, 364, 366, 367, 383; 544/360, 364, 366, 367, 383

(56) References Cited

U.S. PATENT DOCUMENTS

| | | | |
|---|---|---|---|
| 3,920,660 A | 11/1975 | Fontanella et al. | ... 250/250 BC |
| 5,352,461 A | 10/1994 | Feldstein et al. | ........... 424/493 |
| 5,700,804 A | 12/1997 | Collins et al. | ............... 514/255 |
| 5,750,530 A | 5/1998 | Bryans et al. | ............... 514/255 |
| 5,817,751 A | 10/1998 | Szardenings et al. | ....... 530/317 |
| 5,861,380 A | 1/1999 | Gyorkos et al. | ............... 514/19 |
| 5,891,877 A | 4/1999 | Brocchini et al. | ....... 514/235.8 |
| 5,902,812 A | 5/1999 | Brocchini et al. | .......... 514/253 |
| 5,932,579 A | 8/1999 | Campbell et al. | ........... 514/249 |
| 6,046,197 A | 4/2000 | Bhatnagar et al. | .......... 514/249 |
| 6,046,198 A | 4/2000 | Bhatnagar et al. | .......... 514/249 |

FOREIGN PATENT DOCUMENTS

| | | |
|---|---|---|
| JP | 2000-327575 A | 11/2000 |
| WO | WO 96/00391 | 1/1996 |
| WO | WO 97/18214 | 5/1997 |
| WO | WO 02/11676 | 2/2002 |

OTHER PUBLICATIONS

Ahuja and Murphy, "The *CXC* Chemokines Growth–regulated Oncogene (GRO) α, GROβ, GROγ, Neutrophil–activating Peptide–2, and Epithelial Cell–derived Neutrophil–activating Peptide–78 Are Potent Agonists for the Type B, but Not the Type A, Human Interleukin–8 Receptor," *J. Biol. Chem.* 271: 20545, 1996.

Baglioni et al., "Binding of Human Tumor Necrosis Factor to High Affinity Receptors on HeLa and Lymphoblastoid Cells Sensitive to Growth Inhibition," *The Journal of Biological Chemistry* 260(25): 13395–13397, Nov. 5, 1985.

Karlsson et al., "Biosensor Analysis of Drug–Target Interactions: Direct and Competitive Binding Assays for Investigation of Interactions between Thrombin and Thrombin Inhibitors," *Analytical Biochemistry* 278: 1–13, 2000.

Last–Barney et al., "Synergistic and Overlapping Activities of Tumor Necrosis Factor–α and IL–1," *The Journal of Immunology* 141(2): 527–530, Jul. 15, 1988.

Shimizu et al., "High–performance affinity beads for identifying drug receptors," *Nature Biotechnology* 18: 877–881, Aug. 2000.

English Abstract of JP 2000–327575A, esp@cenet, ep.espacenet.com.

WPI Database, Section Ch, Week 200121, Accession No. 2001–205081.

Bianco et al., "Solid–phase synthesis and structural characterization of highly substituted hydroxyproline–based 2,5–diketopiperazines," *J Org Chem.* 65(7):2179–2187, Apr. 7, 2000.

*Primary Examiner*—Mary E. Ceperley
(74) *Attorney, Agent, or Firm*—Davis Wright Tramaine LLP; Jane E. R. Rotter

(57) ABSTRACT

The synthesis of novel diketopiperazines, their use in inhibiting cellular events such as those involving NFK-α, NFK-β and in the treatment of inflammation events, a combinatorial library of diverse diketopiperazines and process for their synthesis as a library and as individual compounds. In particular novel diketopiperazines are disclosed including their synthesis and use in cellular events such as activation of the transcription factor, nuclear factor, TNF-α, TNF-β and also apoptosis.

30 Claims, 8 Drawing Sheets

Legend: (a) Tentagel SRAM, PyAOP, NMM, NMP; (b) Tentagel SRAM-amino acid-NH₂, PyAOP, NMM, NMP; (c) piperidine, NMP; (d) i) R¹²CO₂H, ii) HATU, NMM, NMP; (e) Pd[P(Ph)₃]₄, HN(Me)Ph, CHCl₃; (f) i) HATU, NMM, NMP, ii) H-R¹³; (g) TFA/H₂O (9:1 v/v).

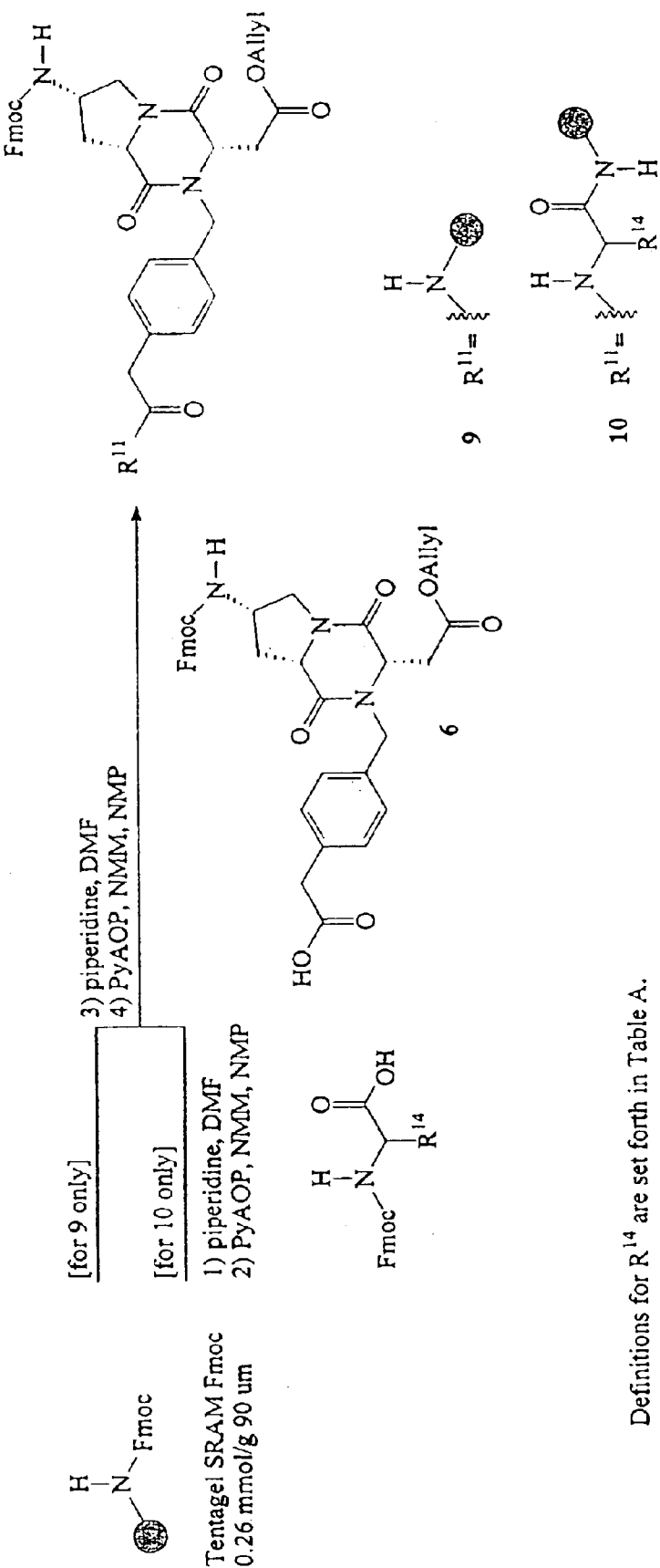

Definitions for $R^{12}$ are set forth in Table B.

Definitions for R[13] are set forth in Table C.

PHARMACEUTICAL USES AND SYNTHESIS OF DIKETOPIPERAZINES

This application claims the benefit of U.S. Provisional Patent Application No. 60/259,359, filed Dec. 29, 2000, where this provisional application is incorporated herein by reference in its entirety.

TECHNICAL FIELD

In general, this application is directed to novel diketopiperazines, their use in inhibiting cellular events involving TNF-α, e.g., NFK-α and/or NFK-β, IL-8, GRO-α, CXCR1, CXCR2 and treatment of inflammation events in general.

BACKGROUND OF THE INVENTION

The process of discovering new therapeutically active compounds for a given indication often involves the screening of compounds from available compound collections. From the compounds tested one or more structures is selected as a promising lead. A number of related analogues are then synthesized in order to develop a structure-activity relationship and select one or more optimal compounds. Following traditional one-at-a-time synthesis and biological testing of analogues, this optimization process is time consuming and labor intensive. Adding significant numbers of new structures to the compound collections used in this initial screening step of the discovery and optimization process cannot be accomplished with traditional one-at-a-time synthesis methods, except over a time frame of months or even years. Faster methods are needed that allow for the preparation of libraries of related compounds in a matter of days or a few weeks. This need is particularly evident when it comes to synthesizing more complex compounds, such as diketopiperazines.

Combinatorial approaches have recently been extended to "organic" or non-peptide, libraries. There is a need in the art for new and diverse organic libraries, which may be used in screening processes.

Although treatment regimens are available for the symptomatic amelioration of diseases such as rheumatoid arthritis, asthma, inflammatory bowel disease, allergic inflammation of respiratory pathways, cancer, atherosclerosis, sepsis, adult respiratory distress syndrome, reperfusion injury, graft vs. host disease, multiple sclerosis, severe invasive infections such as fulminant hepatitis, AIDS and bacterial meningitis, there still exists the need for a composition and method for preventing and/or treating the inflammation which is often associated with the disease.

This invention satisfies these needs and provides related advantages as well. The present invention overcomes the known limitations to classical organic synthesis of diketopiperazines, the shortcomings of combinatorial chemistry as directed to diketopiperazines, and provides compounds which are useful in inhibiting TNF-α, TNF-β, Il-8 and apoptotic mediated processes, and other inflammation-resultant situations. Moreover, this invention provides a library of diverse diketopiperazines useful in elucidating structure-function relationships in biological processes, such as inflammation.

SUMMARY OF THE INVENTION

In one aspect, the present invention provides a diketopiperazine (DKP) compound of the structure (I):

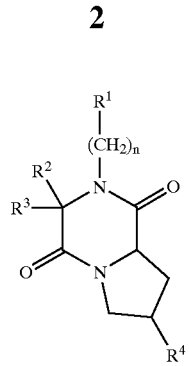

and optical isomers, diastereomers, enantiomers and pharmaceutically acceptable salts thereof in isolation or mixture, where, independently at each location: $R^1$ is an aryl or heteroaryl ring; $R^2$ and $R^3$ are selected from hydrogen, alkyl, heteroalkyl, aryl, heteroaryl, carbocycle aliphatic ring, and heterocycle aliphatic ring; n is 1, 2 or 3; $R^4$ is selected from —$OR^5$ and —$NR^6R^7$, $R^5$ is selected from hydrogen, alkyl, heteroalkyl, aryl, heteroaryl, carbocycle aliphatic ring and heterocycle aliphatic ring; and $R^6$ and $R^7$ are independently selected from hydrogen, alkyl heteroalkyl, aryl, heteroaryl, carbocycle aliphatic ring and heterocycle aliphatic ring or $R^6$ and $R^7$ taken together with the nitrogen atom to which they are attached form a heterocycle aliphatic ring.

In other aspects, the present invention provides a DKP compound of structure (1) wherein $R^1$ is phenyl and the phenyl is substituted with 1–4 substituents independently selected at each occurrence from alkyl, heteroalkyl, aryl, heteroaryl, carbocycle aliphatic ring, heterocycle aliphatic ring. In other aspects, the present invention provides a DKP compound of structure (1) wherein $R^1$ is phenyl having a substituent at the position para to the site of attachment to the piperazine ring.

In other aspects, the present invention provides a DKP compound of structure (1) wherein $R^1$ is phenyl having a substituent at the position para to the site of attachment to the piperazine ring, and the substituent has the formula $R^{10}$—$R^9$—$R^8$—, wherein $R^8$ is selected from direct bond, alkylene and haloalkylene; $R^9$ is selected from direct bond and carbonyl, and $R^{10}$ is selected from hydrogen, $R^{11}$—O—, $(R^{11})_2N$— and $R^{11}$—(C=O)—NH—, wherein $R^{11}$ is selected from hydrogen and organic groups having 1–20 carbons and optionally containing 1–4 heteroatoms selected from oxygen and nitrogen. In a further aspect, $R^8$ is methylene; $R^9$ is carbonyl, and $R^{10}$ is $(R^{11})_2N$— wherein $R^{11}$ is selected from hydrogen and organic groups having 1–20 carbons and optionally containing 1–4 heteroatoms selected from oxygen and nitrogen.

In other aspects, the present invention provides a DKP compound of structure (1) wherein $R^1$ is phenyl having a substituent at the position para to the site of attachment to the piperazine ring, and the substituent has the formula

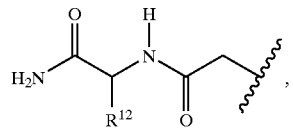

wherein $R^{12}$ is selected from hydrogen and organic groups having 1–20 carbons and optionally containing 1–4 heteroatoms selected from oxygen and nitrogen. In a further aspect, $R^{12}$ is selected from hydrogen, alkyl, heteroalkyl, aryl, heteroaryl, carbocycle aliphatic ring and heterocycle aliphatic ring. The $R^{12}$ group may, optionally be selected from the following twelve exemplary formulae:

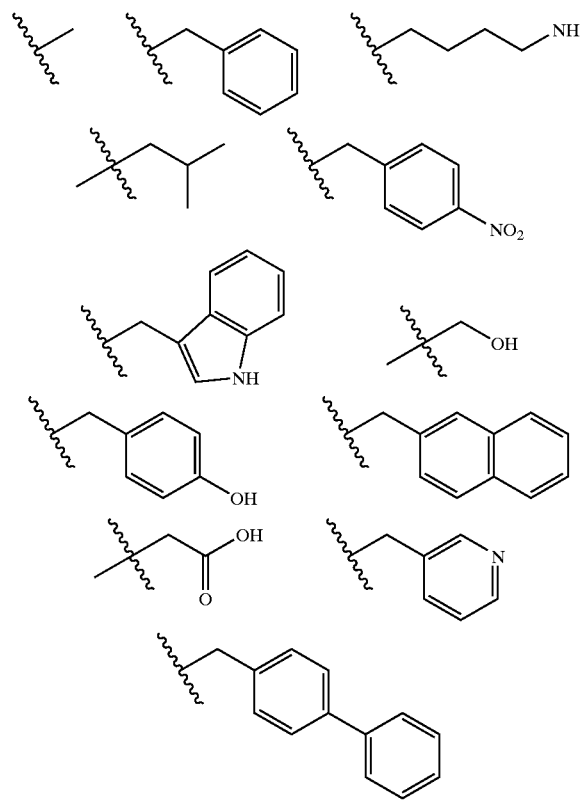

In other aspects, the present invention provides a DKP compound wherein $R^1$ is phenyl. Optionally, in any of the above-described aspects, n is 1. Optionally, in any of the above-described aspects, $R^2$ and $R^3$ are independently selected from groups of the formula $R^{10}$—$R^9$—$R^8$—, wherein $R^8$ is selected from direct bond, alkylene and haloalkylene; $R^9$ is selected from direct bond and carbonyl, and $R^{10}$ is selected from hydrogen, $R^{11}$—O—, $(R^{11})_2N$— and $R^{11}$—(C=O)—NH—, wherein $R^{11}$ is selected from hydrogen and organic groups having 1–20 carbons and optionally containing 1–4 heteroatoms selected from oxygen and nitrogen, with the proviso that two $R^{11}$ groups bonded to the same nitrogen may be bonded together so as to form a heterocyclic ring with the common nitrogen. In one further aspect, $R^8$ is methylene; $R^9$ is selected carbonyl, and $R^{10}$ is $(R^{11})_2N$—. For instance, $R^{10}$ may be selected from the following twelve exemplary formulae:

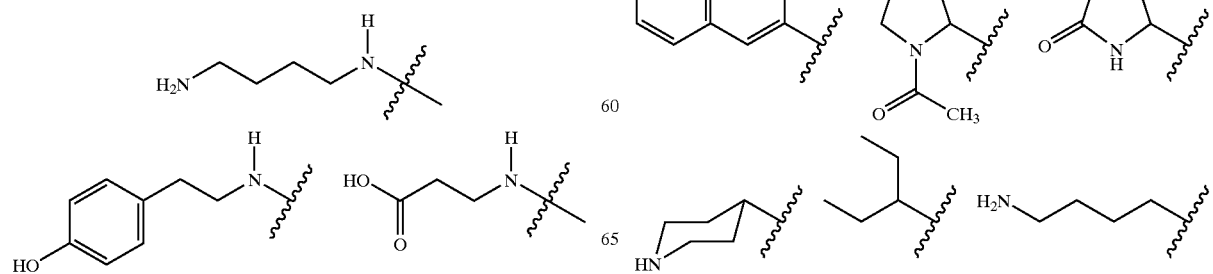

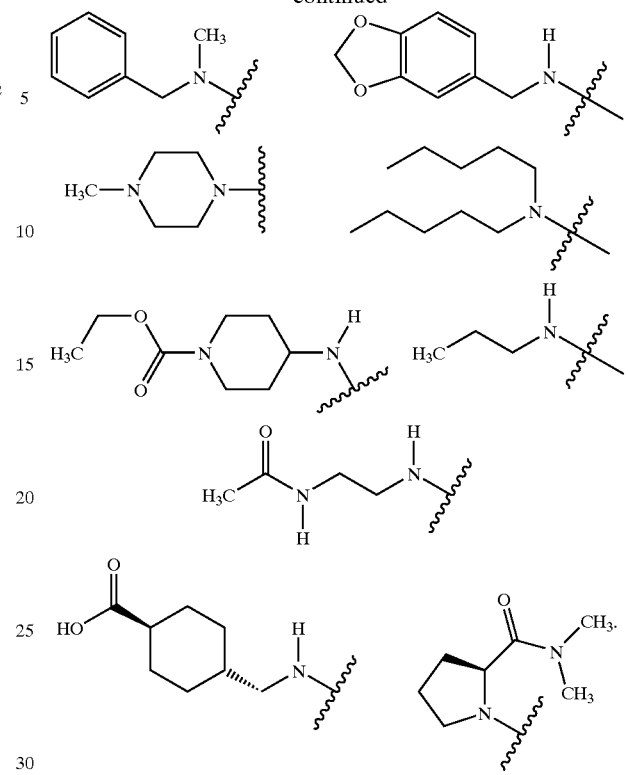

Optionally, in any of the above-described aspects, $R^4$ is —$OR^5$. The $R^5$ may, in one aspect, be selected from hydrogen and alkyl. Optionally, in any of the above-described aspects, and unless otherwise inconsistent, $R^4$ is —NR $R^7$. The $R^6$ may be hydrogen and $R^7$ may be $R^{13}$—C(=O)— where $R^{13}$ is selected from the following twelve exemplary formulae:

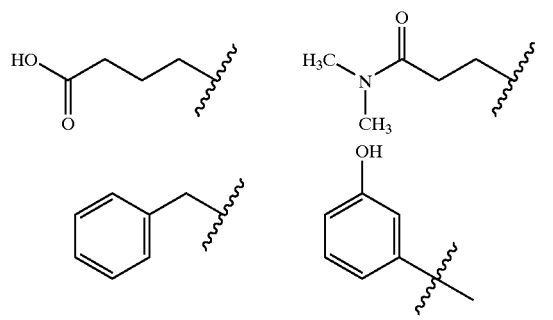

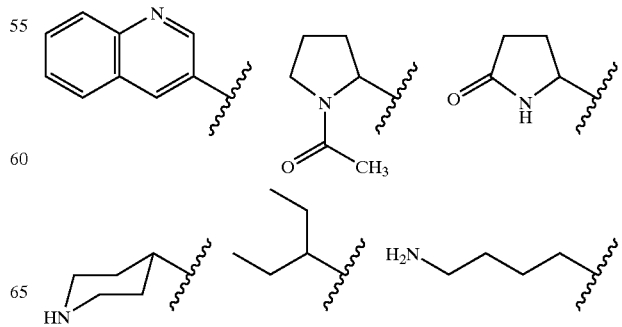

-continued

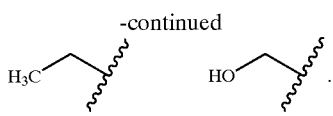

In another aspect, the present invention provides a composition comprising a DKP compound according to any of the aspects described above and herein, and a pharmaceutically acceptable adjuvant, carrier, diluent or excipient.

In another aspect, the present invention provides a method of treating inflammation comprising administering to a subject in need thereof a therapeutically effective amount of a DKP compound as set forth herein.

In another aspect, the present invention provides a method for inhibiting a TNF-α mediated processes, comprising administering to a patient in need thereof, through a therapeutically or prophylactically acceptable manner, a therapeutically or pharmaceutically effective amount of a composition comprising a DKP compound as set forth herein.

In another aspect, the present invention provides a method for inhibiting a TNF-α. mediated processes, comprising administering to a patient in need thereof, through a therapeutically or prophylactically acceptable manner, a therapeutically or pharmaceutically effective amount of a composition comprising a DKP compound as set forth herein, wherein the administering is selected from, for example, transdermal, oral, intravenous, intramuscular, vaginal, rectal, pulmonary, subcutaneous, sublingual and transmucosal administration.

In another aspect, the present invention provides a method for inhibiting a TNF-α. mediated processes, comprising administering to a patient in need thereof, through a therapeutically or prophylactically acceptable manner, a therapeutically or pharmaceutically effective amount of a composition comprising a DKP compound as set forth herein.

In another aspect, the present invention provides a method for treating a condition associated with an elevated level of NFκB activity in a subject, comprising administering to a subject in need thereof an amount of a DKP compound effective to lower the NFκB activity, wherein the DKP compound is described herein.

In another aspect, the present invention provides a method for treating a condition associated with an elevated level of NFκB activity in a subject, comprising administering to a subject in need thereof an amount of a DKP compound effective to lower the NFκB activity, wherein the DKP compound has the formula (1) as set forth above, according to any of the aspects disclosed herein.

In another aspect, the present invention provides a method of inhibiting IL-8 production in a subject in need thereof comprising administering to the subject an effective amount of a DKP compound as set forth herein.

In another aspect, the present invention provides a method of inhibiting GRO-α. production in a subject in need thereof comprising administering to the subject an effective amount of a DKP compound as set forth herein.

In another aspect, the present invention provides a method for inhibiting a CXCR1 and/or CXCR2 mediated processes, comprising administering to a patient in need thereof, through a therapeutically or prophylactically acceptable manner, a therapeutically or pharmaceutically effective amount of a composition comprising a DKP compound as set forth herein according to any of the aspects of the present invention. In one further aspect, the method inhibits a CXCR1 mediated processes, while in another aspect the method inhibits a CXCR2 mediated processes.

In another aspect, the present invention provides a method for treating an inflammation event, comprising administering to a patient in need thereof, through a therapeutically or prophylactically acceptable manner, a therapeutically or pharmaceutically effective amount of a composition comprising a DKP compound as set forth herein, including any of the aspects of the present invention.

In any of the foregoing methods, the administering may be selected from transdermal, oral, intravenous, intramuscular, vaginal, rectal, pulmonary, subcutaneous, sublingual and transmucosal administration.

In another aspect, the present invention provides a method for identifying a binding partner to a DKP compound according to any of the aspects described herein, comprising: immobilizing proteins known to be involved in the TNF-α signaling pathway onto a suitable carrier; and passing a solution of said compounds in isolation or mixture over said proteins and analyzing for compound:protein complex formation using surface plasmon resonance (SPR). This method may be conducted in a manner similar to that reported by Karlsson, R et al. Biosensor Analysis of Drug-Target Interactions: Direct and Competitive Binding Assays for Investigation of Interactions Between Thrombin and Thrombin Inhibitors. Anal. Biochem. 2000, 278(1), 1–13. For other examples of identifying small molecule-protein interactions using SPR see the Biacore website at WorldWideWeb.biocore.com.

In another aspect the present invention provides a method for identifying a binding partner to a DKP compound according to any of the aspects disclosed herein, comprising: contacting a cell or cell components with said solid phase compounds in isolation or mixture; removing uncomplexed cellular material, for example by gentle washing with aqueous buffer; and recovering said binding partner from the solid phase compounds. This method may be conducted in a manner similar to that reported by Shimizu, N et al. High Performance Affinity Beads for Identifying Drug Receptors. *Nature Biotechnology*, 2000, 18(8), 877–881).

These and other aspects of the present invention are described more fully herein, in some instances by reference to the following drawings.

BRIEF DESCRIPTION OF THE DRAWINGS

FIGS. 5, 6 and 7 provide additional details regarding the synthetic scheme shown in FIG. 2.

DETAILED DESCRIPTION OF THE INVENTION

Figure 1:
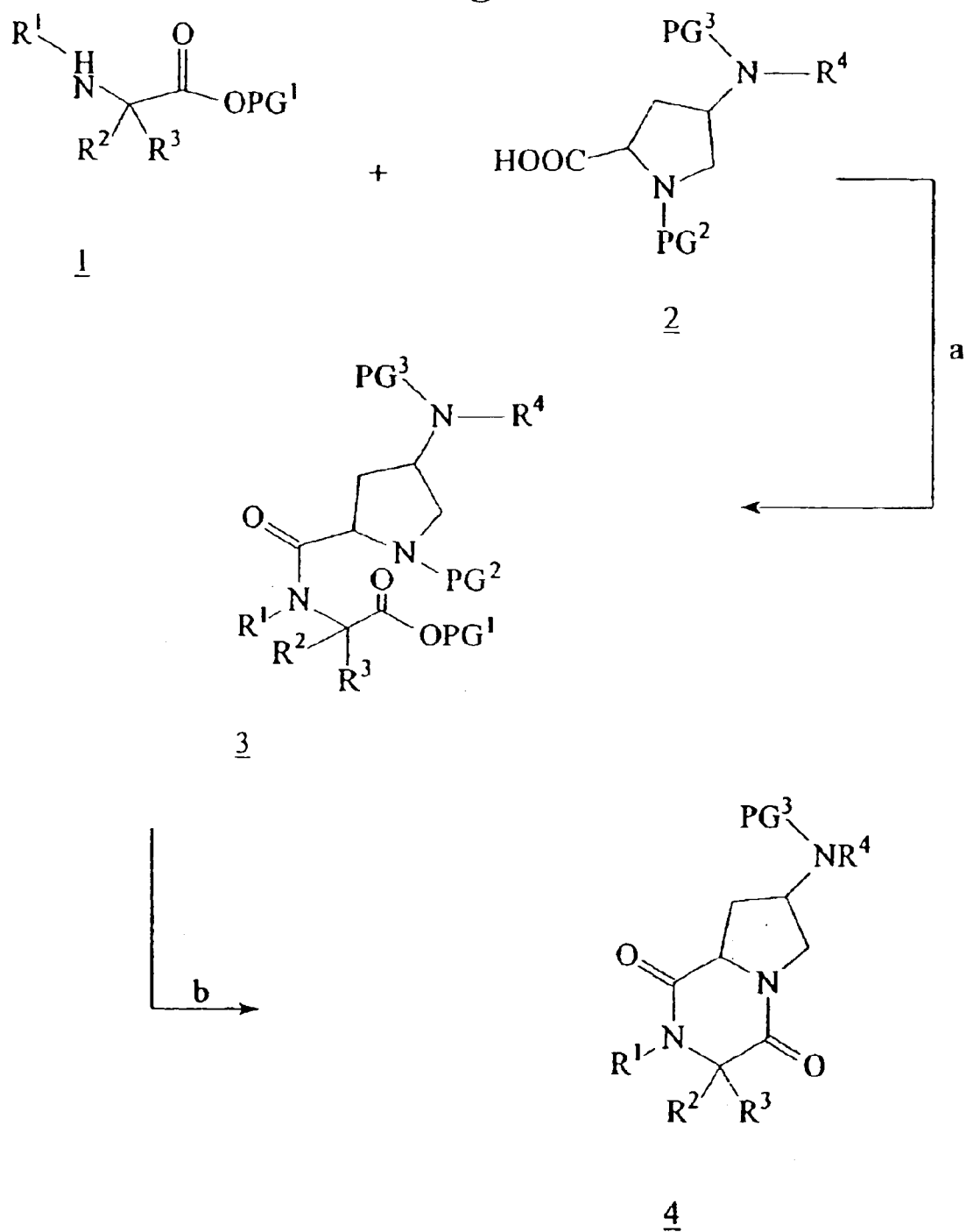
FIG. 1 summarizes a two-step general synthetic scheme to prepare a diketopiperazine (DKP) compound from two starting materials, where the compound may be elaborated to provide additional DKP compounds of the present invention.

The present invention provides: diketopiperazine (DKP) compounds, including optical isomers, diastereomers, enantiomers, solvates, polymorphs, and pharmaceutically acceptable salts thereof in isolation or mixture; methodology for preparing DKP compounds in solution, on a solid support, individually, and in a library format; compositions comprising a DKP compound and a pharmaceutically acceptable adjuvant, carrier, diluent and/or excipient; compositions comprising a plurality of DKP compounds, particularly in a library format; methods of inhibiting cellular events involving TNFα, e.g., NFK-α and/or NFK-β, IL-8, GRO-α, CXCR1 and CXCR2, using DKP compounds; methods of treatment of inflammation events in general using DKP compounds; and additional uses of DKP compounds as described herein.

Before providing a more detailed description of the present invention, a number of terms as used herein are defined as follows:

Definition of Terms

As used herein, the following terms have the indicated meanings.

The singular forms "a", "and", and "the" include plural referents unless the context clearly dictates otherwise. For example, "a compound" refers to one or more of such compounds.

"Alkyl" is a saturated or unsaturated, straight or branched, hydrocarbon chain. In various embodiments, the alkyl group has 1–18 carbon atoms, i.e., is a C1–C18 group, or is a C1–C12 group, a C1–C6 group, or a C1–C4 group. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Alkyl chains may be substituted or unsubstituted. In one embodiment, the alkyl chains are unsubstituted. In another embodiment, the alkyl chain is substituted, e.g., with 1 substituent (i.e., the alkyl group is monosubstituted), or 1–2 substituents, or 1–3 substituents, or 1–4 substituents, etc.

"Aryl" is an aromatic hydrocarbon ring system. The ring system may be monocyclic or fused polycyclic (e.g., bicyclic, tricyclic, etc.). In various embodiments, the monocyclic aryl ring is C5–C10, or C5–C7, or C5–C6, where these carbon numbers refer to the number of carbon atoms that make up the ring system. A C6 ring system, i.e., a phenyl ring, is a preferred aryl ring. In various embodiments, the polycyclic ring is a bicyclic aryl ring, where preferred bicyclic aryl rings are C8–C12, or C9–C10. A naphthyl ring, which has 10 carbon atoms, is a preferred polycyclic aryl ring. Aryl rings may be substituted or unsubstituted. In one embodiment, the aryl ring is unsubstituted. In another embodiment, the aryl ring is substituted with 1 substituent (i.e., the aryl ring is monosubstituted), or 1–2 substituents, or 1–3 substituents, or 1–4 substituents, etc.

"Carbocyclic aliphatic ring," also referred to as carbocycle, is a saturated or unsaturated, monocyclic or polycyclic (e.g., bicyclic, tricyclic, etc.) hydrocarbon ring. Carbocyclic aliphatic rings are not aromatic. A polycyclic hydrocarbon ring may include fused, spiro or bridged ring structures. In various embodiments, the monocyclic carbocyclic aliphatic ring is a C3–C10, or a C4–C7, or a C5–C6 ring system. In various embodiments, the polycyclic carbocyclic aliphatic ring is a C6–C12, or a C9–C10 ring system. In one embodiment, the polycyclic ring is bicyclic. In another embodiment, the polycyclic ring is bicyclic or tricyclic. Carbocyclic aliphatic rings include cyclopropyl, cyclopentyl, cyclohexyl, cyclohexenyl, cycloheptyl, and cyclooctyl. Carbocycles may be substituted or unsubstituted. In one embodiment, the carbocycle is unsubstituted. In another embodiment, the carbocycle is substituted with, e.g., 1 substituent (i.e., the alkyl group is monosubstituted), or 1–2 substituents, or 1–3 substituents, or 1–4 substituents, etc.

"Haloalkyl" is an alkyl chain substituted with one or more halogens. A preferred haloalkyl is trifluoromethyl.

"Heteroalkyl" is a saturated or unsaturated, straight or branched, chain alkyl group wherein at least one carbon is replaced with a heteroatom. The heteroalkyl group may, in various embodiments, have one heteroatom, or 1–2 heteroatoms, or 1–3 heteroatoms, or 1–4 heteroatoms. Heteroalkyl chains may contain from 1 to 18 (i.e., 1–18) member atoms (carbon and heteroatoms) in the chain, and in various embodiments contain 1–12, or 1–6, or 1–4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted. As another example, trifluoromethyl is a heteroalkyl group wherein the three methyl groups of a t-butyl group are replaced by fluorine.

"Heteroaryl" is an aromatic ring system or a semi-aromatic system of rings or a pseudo aromatic ring or rings containing carbon and at least one heteroatom in at least one of the rings. The heteroaryl group may, in various embodiments, have one heteroatom, or 1–2 heteroatoms, or 1–3 heteroatoms, or 1–4 heteroatoms in the ring. The heteroaryl group may further include more than one ring system, which in various embodiments may include one heteroatom or 1–2 heteroatoms, or 1–3 heteroatoms, or 1 heteroatom in each ring system, or 1–4 heteroatoms in each ring system. The heteroaryl group which comprises more than one ring system may, in various embodiments, have one or more than one of the ring systems aromatic. Heteroaryl rings may be monocyclic or polycyclic, where the polycyclic ring may contained fused, spiro or bridged ring junctions. In one embodiment, the heteroaryl is selected from monocyclic and bicyclic. Monocyclic heteroaryl rings may contain from about 5 to about 10 member atoms (carbon and heteroatoms), preferably from 5–7, and most preferably from 5–6 member atoms in the ring. Bicyclic heteroaryl rings may contain from about 8–12 member atoms, or 9–10 member atoms in the ring. The heteroaryl ring may be unsubstituted or substituted. In one embodiment, the heteroaryl ring is unsubstituted. In another embodiment, the heteroaryl ring is substituted. In one aspect, the heteroaryl ring may contain 1 substituent. In another aspect, the heteroaryl ring contains 1–2 substituents. In another aspect, the heteroaryl ring contains 1–3 substituents. In another aspect, the heteroaryl ring contains 1–4 substituents, etc. Exemplary heteroaryl rings include benzofuran, benzothiophene, furan, imidazole, indole, isothiazole, oxazole, pyrazine, pyrazole, pyridazine, pyridine, pyrimidine, pyrrole, quinoline, thiazole and thiophene.

"Heteroatom" is a halogen, nitrogen, sulfur, or oxygen atom. Groups containing more than one heteroatom may contain different heteroatoms.

"Heterocyclic aliphatic ring," also referred to as "heterocyclyl", is a saturated or unsaturated, monocyclic or polycyclic (e.g., bicyclic, tricyclic, etc.) ring containing carbon and at least one heteroatom selected from nitrogen, oxygen and sulfur. Heterocyclic aliphatic rings are not aromatic per se but may be pseudo-aromatic and/or readily be made aromatic through methods known in the art. The heterocyclic aliphatic ring may, in various embodiments, have one heteroatom, or 1–2 heteroatoms, or 1–3 heteroatoms, or 1–4 heteroatoms, etc. In one embodiment, the heterocyclic aliphatic ring is monocyclic, where the monocyclic ring may have 3–10, or 4–7, or 5–6 member atoms. In another embodiment, the heterocyclic aliphatic ring is polycyclic, where in various embodiments, the ring may be bicyclic, or may be tricyclic, or may be either bicyclic or tricyclic. A polycyclic ring system may have one or more fused, spiro or bridged ring systems. The polycyclic heterocyclic aliphatic ring system may have 6–12, or 9–10 member atoms. The heterocyclic ring may be unsubstituted or substituted. In one embodiment, the heterocyclic ring is unsubstituted. In another embodiment, the heterocyclic ring is substituted. The substituted heterocyclic ring may contain 1 substituent, or 1–2 substituents, or 1–3 substituents, or 1–4 substituents, etc. Exemplary heterocyclic aliphatic rings include piperazyl, morpholinyl, tetrahydrofuranyl, tetrahydropyranyl and piperidyl.

"Lower alkyl" is an alkyl chain comprised of 1–6, preferably 1–4 carbon atoms.

"Pharmaceutically acceptable salt" and "salts thereof" means organic or inorganic salts of the pharmaceutically important molecule. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically important organic molecule may have more than one charged atom in its structure. Situations where multiple charged atoms are part of the molecule may have multiple counterions. Hence, the molecule of a pharmaceutically acceptable salt may contain one or more than one charged atoms and may also contain, one or more than one counterion. The desired charge distribution is determined according to methods of drug administration. Examples of pharmaceutically acceptable salts are well known in the art but, without limiting the scope of the present invention, exemplary presentations can be found in the Physician's Desk Reference, The Merck Index, The Pharmacopoeia and Goodman & Gilman's The Pharmacological Basis of Therapeutics.

"Substituents" replace one or more hydrogen atoms with a non-hydrogen atom on an alkyl, heteroalkyl, aryl, heteroaryl, carbocycle, and/or heterocyclyl group as defined herein. Where the substituent contains a heteroatom, that heteroatom may be at any oxidation state, e.g., sulfur as part of a substituent may vary from an oxidation state of −2 to +8, and may be part of a complex or chelate as in a sulfoxide a mercapto-phosphine or metal chelated in a thia-crown ether. Suitable substituents that may be located on one or more of these groups include the following: halogen, alkoxy (i.e., alkyl-O—, e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, alkyloxycarbonyloxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di-C1–C3 alkanylamino, methylphenylamino, methylbenzylamino, C1–C3 alkanylamido, acylamino, carbamamido, ureido, guanidino, nitro and cyano). Additional substituents include alkyl (e.g., $C_1$–$C_6$alkyl), heteroalkyl (e.g., $C_1$–$C_6$alkoxy, —$CH_2C(=O)NH_2$, N-substituted —$CH_2C(=O)NH_2$ groups, e.g., —$CH_2C(=O)NH$(alkyl), —$CH_2C(=O)NH$(heteroalkyl), and N,N-disubstituted —$CH_2C(=O)NH_2$ groups, e.g., —$CH_2C(=O)N$(alkyl)$_2$, —$CH_2C(=O)N$(heteroalkyl)$_2$, —$CH_2C(=O)N$(alkyl)(heteroalkyl), carboxyl, carbonyl($C_1$–$C_6$)alkoxy, halogen, hydroxyl, nitro, —$SO_3H$, amino), and arylheteroalkylene (e.g., (2,4,6-trimethoxyphenyl)—$CH_2$—N—C(=O)—$CH_2$—), to name a few. Moreover, any substituent may have from 1–5 further substituents attached thereto.

"Amino" means a trivalent amine substituted with up to 2 alkyl groups as defined above or with 1 alkyl group and a hydrogen group, or with one aryl and one alkyl groups, or with two aryl groups, or with two or more hydrogen groups or with the substitution required to complete the nitrogen's valence requirements. "Amino" further includes amino salts where the nitrogen is hypervalent, having four bonds and may or may not have a charge and a counterion. The counterion, when present, may be an external inorganic and/or organic counterion and/or may be an internal counterion. Inorganic counterions include, for example, anions such as halo anions and other non-metal anions. Examples of organic counterions include, for example, anionic organic moieties such as acetate, citrate and other anionic organic moieties. Moreover, any combination of groups may be combined, e.g., alkyl-aryl-heteroaryl-amino-carbocycle . . . etc.

As used herein and in the appended claims a "library" means a large number of chemical derivatives used in screening for biological activity or other activity. In general a library will have greater than 20 members, preferably the library will have at least 50 members, more preferably the library will have at least 96 members and most preferably the library will have at least 1000 members.

As used herein and in the appended claims "scaffold" means a common chemical structure found within a library of organic compounds. Similarly, within a combinatorial chemical library the scaffold forms the basis for a diverse series of chemical derivatization, additions and subtractions. Importantly, regardless of the extent of the chemical derivatization performed on the scaffold, the product is within the scope of the combinatorial library.

"Inflammation event" or "inflammation" or "swelling" are synonymous terms that mean an abnormal enlargement of a portion or tissue of an animal. The abnormal enlargement may be the normal, expected result of another event, such as, for example, sepsis, fever, trauma, shock, or injury. Non-limiting examples of some of these events include sepsis due to renal or liver failure, fever secondary to systemic infection, localized fever secondary to local infection, blunt force trauma or emotional trauma having physical manifestations, shock secondary to trauma and/or other events causing a pooling of body fluids and an injury causing release of cellular fluids initiating the inflammation cascade.

As used herein, "compounds described in the chemical literature" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., at their website at WorldWideWeb.acs.org may be contacted for more details). Chemicals that are known but not commercially available in catalogs may be prepared by custom chemical synthesis houses, where many of the standard chemical supply houses (e.g., those listed above) provide custom synthesis services.

As used herein "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

All other acronyms and abbreviations have the corresponding meaning as published in journals relative to the art of organic chemistry.

A. Compounds

In one aspect, the present invention provides a diketopiperazine (DKP) compound of the structure (I):

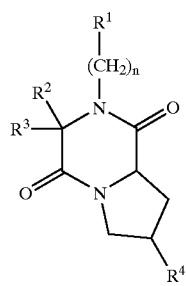

(I)

and optical isomers, diastereomers, enantiomers and pharmaceutically acceptable salts thereof in isolation or mixture, where, independently at each location: $R^1$ is an aryl or heteroaryl ring; $R^2$ and $R^3$ are selected from hydrogen, alkyl, heteroalkyl, aryl, heteroaryl, carbocycle aliphatic ring, and heterocycle aliphatic ring; n is 1, 2 or 3; $R^4$ is selected from —OR and —NR $R^6R^7$, $R^5$ is selected from hydrogen, alkyl, heteroalkyl, aryl, heteroaryl, carbocycle aliphatic ring and heterocycle aliphatic ring; and $R^6$ and $R^7$ are independently selected from hydrogen, alkyl, heteroalkyl, aryl, heteroaryl, carbocycle aliphatic ring and heterocycle aliphatic ring or $R^6$ and $R^7$ taken together with the nitrogen atom to which they are attached form a heterocycle aliphatic ring.

In other aspects, the present invention provides a DKP compound of structure (1) wherein $R^1$ is phenyl and the phenyl is substituted with 1–4 substituents independently selected at each occurrence from alkyl, heteroalkyl, aryl, heteroaryl, carbocycle aliphatic ring, heterocycle aliphatic ring. In other aspects, the present invention provides a DKP compound of structure (1) wherein $R^1$ is phenyl having a substituent at the position para to the site of attachment to the piperazine ring.

In other aspects, the present invention provides a DKP compound of structure (1) wherein $R^1$ is phenyl having a substituent at the position para to the site of attachment to the piperazine ring, and the substituent has the formula $R^{10}$—$R^9$—$R^8$—, wherein $R^8$ is selected from direct bond, alkylene and haloalkylene; $R^9$ is selected from direct bond and carbonyl, and $R^{10}$ is selected from hydrogen, $R^{11}$—O—, $(R^{11})_2N$— and $R^{11}$—(C=O)—NH—, wherein $R^{11}$ is selected from hydrogen and organic groups having 1–20 carbons and optionally containing 1–4 heteroatoms selected from oxygen and nitrogen. In a further aspect, $R^8$ is methylene; $R^9$ is carbonyl, and $R^{10}$ is $(R^{11})_2N$— wherein $R^{11}$ is selected from hydrogen and organic groups having 1–20 carbons and optionally containing 1–4 heteroatoms selected from oxygen and nitrogen.

In other aspects, the present invention provides a DKP compound of structure (1) wherein $R^1$ is phenyl having a substituent at the position para to the site of attachment to the piperazine ring, and the substituent has the formula

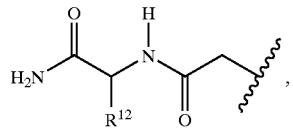

wherein $R^{12}$ is selected from hydrogen and organic groups having 1–20 carbons and optionally containing 1–4 heteroatoms selected from oxygen and nitrogen. In a further aspect, $R^{12}$ is selected from hydrogen, alkyl, heteroalkyl, aryl, heteroaryl, carbocycle aliphatic ring and heterocycle aliphatic ring. The $R^{12}$ group may, optionally be selected from the following twelve exemplary formulae:

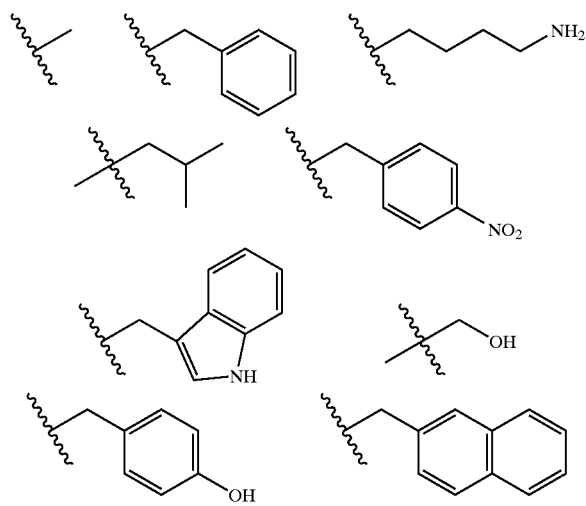

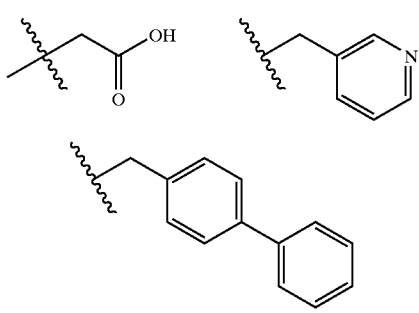
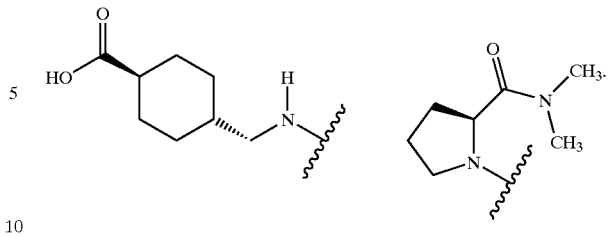

In other aspects, the present invention provides a DKP compound wherein $R^1$ is phenyl. Optionally, in any of the above-described aspects, n is 1. Optionally, in any of the above-described aspects, $R^2$ and $R^3$ are independently selected from groups of the formula $R^{10}$—$R^9$—$R^8$—, wherein $R^8$ is selected from direct bond, alkylene and haloalkylene; $R^9$ is selected from direct bond and carbonyl, and $R^{10}$ is selected from hydrogen, $R^{11}$—O—, $(R^{11})_2$N— and $R^{11}$—(C=O)—NH—, wherein $R^{11}$ is selected from hydrogen and organic groups having 1–20 carbons and optionally containing 1–4 heteroatoms selected from oxygen and nitrogen, with the proviso that two $R^{11}$ groups bonded to the same nitrogen may be bonded together so as to form a heterocyclic ring with the common nitrogen. In one further aspect, $R^8$ is methylene; $R^9$ is selected carbonyl, and $R^{10}$ is $(R^{11})_2$N—. For instance, $R^{10}$ may be selected from the following twelve exemplary formulae:

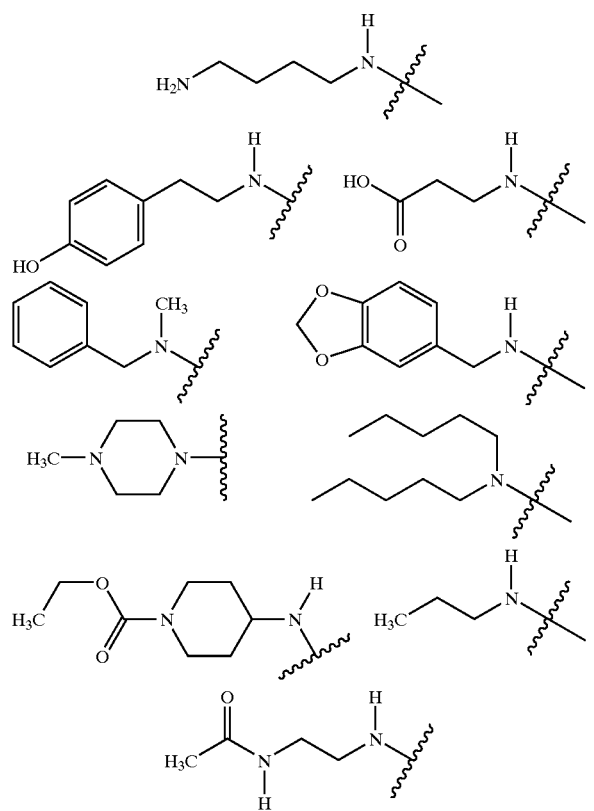

Optionally, in any of the above-described aspects, $R^4$ is —$OR^5$. The $R^5$ may, in one aspect, be selected from hydrogen and alkyl. Optionally, in any of the above-described aspects, and unless otherwise inconsistent, $R^4$ is —$NR^6 R^7$. The $R^6$ may be hydrogen and $R^7$ may be $R^{13}$—C(=O)— where $R^{13}$ is selected from the following twelve exemplary formulae:

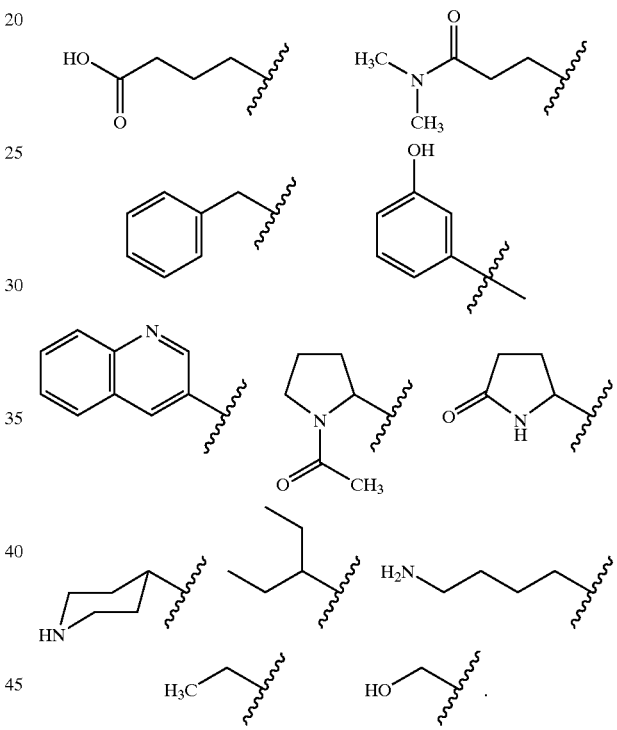

B. Preparation of DKP Compounds

Figure 2:
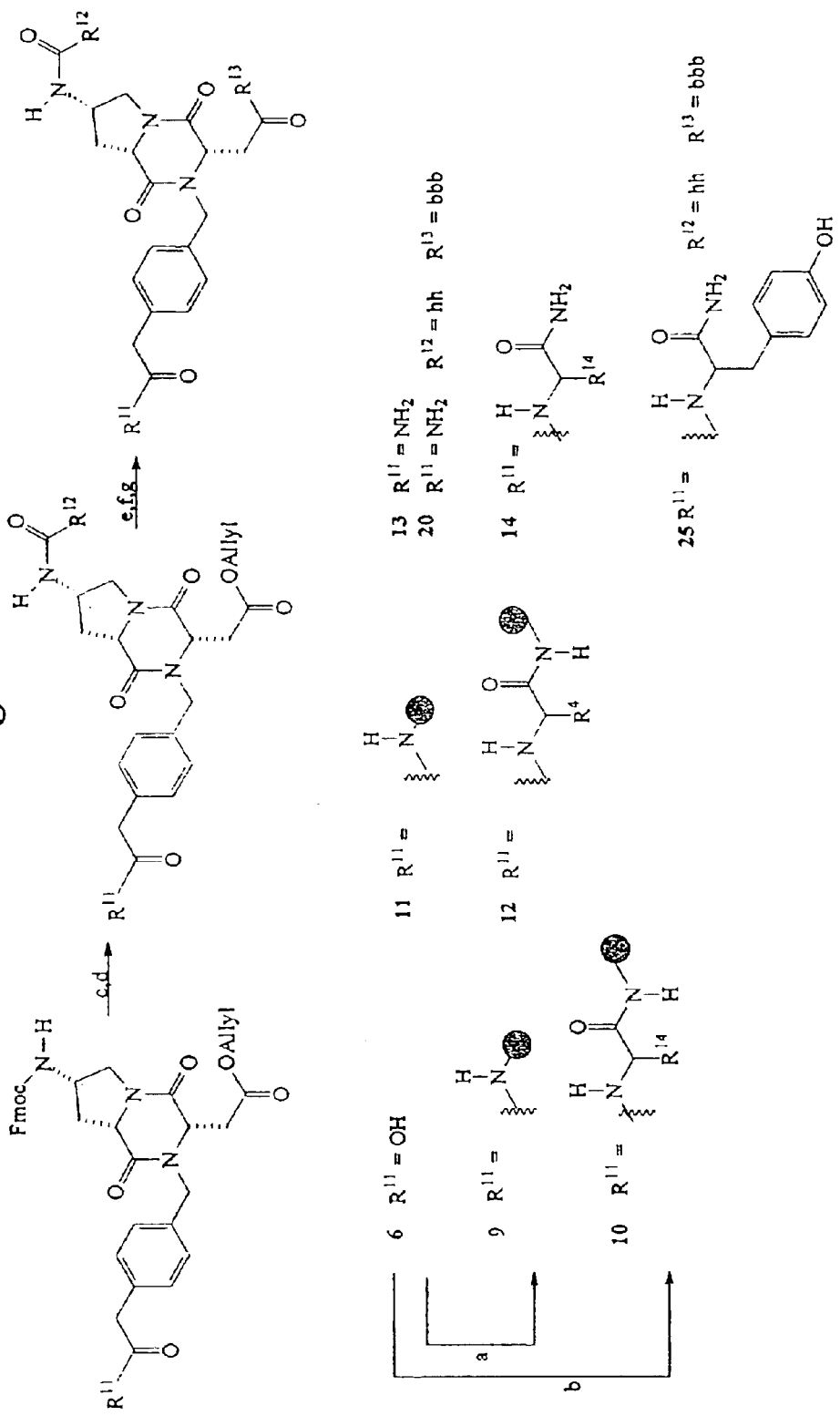
FIG. 2 summarizes a synthetic scheme by which a DKP compound may be bound to a solid support and thereafter elaborated to additional DKP compounds of the present invention.

The DKPs of this invention may be prepared according to FIGS. 1 and 2. In these Figures, protecting groups are denoted by "PG" and are orthogonal to each other unless otherwise indicated.

In FIG. 1, chemical steps (a) and (b) are represented by the following reaction conditions.

(a) is a chemical reaction wherein compound 1 is coupled with compound 2. Suitable conditions for this type of coupling involve performing the reaction in a suitable solvent, e.g., refluxing THF (tetrahydrofuran), in the presence of a coupling agent for amide bond formation and an organoamine base, e.g., PyBrop (bromo-tris-pyrrolidino-phosphonium hexafluorophosphate) and DIEA (diisopropylethylamine).

(b) is a chemical reaction wherein compound 3 is cyclized to form compound 4. Suitable conditions for this type of cyclization involve removal of the protecting group ($PG^2$) from the pyrrolidinyl nitrogen, e.g., Boc (t-butyloxycarbonyl) in TFA(trifluoroacetic acid)/H$_2$O (9:1 v/v), followed by heating the resultant mixture in a suitable solvent such as refluxing DME (dimethoxyethane).

In FIG. 2, a general procedure is disclosed for solid phase synthesis of bicyclic diketopiperazines of the invention, having five steps (a, b, c, d and e) as described below.

Steps (a), (b), or (d)—Coupling of a carboxylic acid to an amine:

Carboxylic acid (ca. 1.2–1.5 eq) is coupled to a support-bound amine group using a suitable coupling agent, e.g., PyAOP (ca. 1.3–1.5 eq) and a base, e.g., NMM (ca. 3–4 eq) and a suitable solvent, e.g., NMP (where typical reaction conditions are rt, 90 min) to generate a support-bound amide group.

Step (c)—Fmoc deprotection:

The amine group of resin-bound protected amine group, e.g., 9-fluorenylmethoxycarbonyl (Fmoc) is deprotected under conditions suitable for the protecting group, e.g. 25% piperidine in NMP (rt) to provide a primary amine group.

Step (e)—Allyl ester deprotection:

A suitably protected carboxylic acid, e.g., an allyl ester of the carboxylic acid, is deprotected under suitable reaction condition, e.g., by addition of a freshly prepared solution of Pd[P(Ph)$_3$]$_4$ and N-methylaniline in CHCl$_3$ (0.025 M and 0.25 M) to generate a carboxylic acid group.

Step (f)—Coupling of an amine to a carboxylic acid:

A resin-bound carboxylic acid group is treated under suitable coupling conditions, e.g., HATU (ca. 1.5 eq) and NMM (ca. 3.8 eq) followed by addition of a primary or secondary amine of the formula $R^{13}$—NH$_2$ (ca. 1.5 eq) in a suitable solvent, e.g., NMP so as to generate an amide group including $R^{13}$.

Step (g)—Final cleavage procedure:

After washing, the resin is treated with acid, e.g., TFA/water (90 :10 v/v). The filtrate is collected and concentrated in vacuo. Crude products are typically afforded in 90–100% of theoretical mass recovery (based on load estimation of the starting resin) and undergo biological assay without further purification.

C. Pharmaceutical Compositions

In another aspect, the present invention provides a composition containing a DKP compound of formula (I) in admixture with a pharmaceutically acceptable adjuvant, carrier, diluent or excipient, i.e., the present invention provides a pharmaceutical composition containing a compound of formula (I). The pharmaceutical composition may contain optional ingredient(s) if desired.

The pharmaceutical compositions of the present invention may be in any form which allows for the composition to be administered to a patient. Typical routes of administration include, without limitation, oral, topical, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of DKP compound in aerosol form may hold a plurality of dosage units.

The composition may be in the form of a solid, liquid or gas (aerosol). In one aspect, the carrier(s) are particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid compositions intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active vanadium(V) complex. Preferred compositions and preparations according to the present invention are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the DKP compounds of the invention and thereby assists in the delivery of the active compound. Suitable agents which may act in this capacity include a monoclonal or polyclonal antibody, a protein or a liposome.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of inflammation.

The pharmaceutical compositions may be prepared by methodology well known in the pharmaceutical art. For example, a composition intended to be administered by injection can be prepared by combining a DKP compounds of formula (I) with water so as to form a solution. A surfactant may be added to facilitate the formation of a homogeneous solution or suspension. Surfactants are compounds that non-covalently interact with the DKP compound so as to facilitate dissolution or homogeneous suspension of the compound in the aqueous delivery system.

D. Biological Applications

The present invention provides DKP, compositions containing a DKP, and methods of using DKP compounds to inhibit cellular events involving TNF-α or IL-8. Thus, in one aspect, the present invention provides a method to modulate binding of TNF-α to cell receptors, and/or modulate the consequential intracellular events comprising administering to a subject in a need thereof an effective amount of a DKP compound of formula (I). The inhibition of TNF-α induced apoptosis and of NFκB activation is one means of preventing and/or treating autoimmune and inflammatory diseases including, but not limited to, rheumatoid arthritis, inflammatory bowel disease, psoriasis, atherosclerosis, asthma, reperfusion injury, ischemia, sepsis, graft vs. host disease, adult respiratory distress syndrome, multiple sclerosis, and a host of severe invasive infections such as fulminant hepatitis, AIDS and bacterial meningitis, and allergic inflammation of the lungs and airways.

Thus, in one aspect, the present invention provides a method of inhibiting TNF-α induced apoptosis comprising administering to a subject in a need thereof an effective amount of a DKP compounds of formula (I). In another aspect, the present invention provides a method of inhibiting NFκB activation comprising administering to a subject in a need thereof an effective amount of a DKP compound of formula (I). In another aspect, the present invention provides a method of inhibiting, preventing, treating, or preventing and/or treating autoimmune and inflammatory diseases including, but not limited to, rheumatoid arthritis, Inflammatory Bowel Disease (IBD), psoriasis, atherosclerosis, asthma, reperfusion injury, ischemia, sepsis, graft vs. host disease, Adult Respiratory Distress Syndrome (ARDS), and multiple sclerosis, comprising administering to a subject in a need thereof an effective amount of a DKP compounds of formula (I). In another aspect, the present invention provides a method of inhibiting, preventing, treating, or preventing and/or treating severe invasive infections such as fulminant hepatitis comprising administering to a subject in a need thereof an effective amount of a DKP compounds of formula (I).

In another aspect, the present invention provides a method for the inhibition of IL-8 or other CXC chemokines binding to CXCR1 and/or CXCR2 receptors comprising administering an effective amount of a compound of formula (I) to a subject in need thereof. In another aspect, the present invention provides a method for reducing the levels of IL-8 within a subject comprising administering to a subject in need thereof an effective amount of a compound of formula (I). In another aspect, the present invention provides a method for treating, preventing, or treating and/or preventing one or more of inflammatory and autoimmune diseases such as Inflammatory Bowel Disease (IBD), psoriasis, rheumatoid arthritis, Acute Respiratory Distress Syndrome (ARDS), cancer, atherosclerosis, reperfusion injury, and graft vs. host disease, comprising administering to a subject in need thereof an effective amount of a compound of formula (I).

The present invention provides a method for inhibiting TNF-α mediated processes, comprising administering to a patient in need thereof, through a therapeutically or prophylactically acceptable manner, a therapeutically or pharmaceutically effective amount of a composition comprising a compound of formula (I). Administering may be by, for example, transdermal, oral, intravenous, intramuscular, vaginal, rectal, pulmonary, subcutaneous, sublingual and transmucosal administration.

The present invention provides a method for treating an inflammation event, comprising administering to a patient in need thereof, through a therapeutically or prophylactically acceptable manner, a therapeutically or pharmaceutically effective amount of a DKP compound of formula (I). Administering may be selected from transdermal, oral, intravenous, intramuscular, vaginal, rectal, pulmonary, subcutaneous, sublingual and transmucosal administration.

The "effective amount" or "therapeutically effective amount" of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In another aspect, the present invention provides a method for identifying a binding partner to a DKP compound as disclosed herein, where the method comprises: immobilizing protein known to be involved in the TNF-α signaling pathway onto a suitable carrier; and passing a solution of said DKP compounds in isolation or mixture over said protein and analyzing for compound:protein complex formation using surface plasmon resonance (SPR). This method may be performed in analogy to the method described in Karlsson, R et al. "Biosensor Analysis of Drug-Target Interactions: Direct and Competitive Binding Assays for Investigation of Interactions Between Thrombin and Thrombin Inhibitors" *Anal. Biochem.* 2000, 278(1), 1–13. For other examples of identifying small molecule-protein interactions using SPR see the Biacore website at WorldWideWeb.biocore.com.

In another aspect, the present invention provides a method for identifying a binding partner to a DKP compound as disclosed herein, where the method comprises: contacting a cell or cell components with said DKP compound in isolation or mixture; removing uncomplexed cellular material, for example by gentle washing with aqueous buffer; and recovering said binding partner from the compounds. The DKP compound(s) are preferably bound to a solid support. See, e.g., methodology reported in Shimizu, N et al. "High Performance Affinity Beads for Identifying Drug Receptors" *Nature Biotechnology*, 2000, 18(8), 877–881).

As to each publication or patent referenced herein, that publication or patent is incorporated herein by reference in its entirety for all purposes.

The following examples are offered by way of illustration, and not by way of limitation.

EXAMPLES

In the following Examples, certain abbreviations are used which have the following meanings. Allyl, 2-propenyl; Boc, tert-butoxycarbonyl; bp, boiling point; DCM, dichloromethane; DIEA, N,N-diisopropylethylamine; DKP, diketopiperazine; DME, 1,2-dimethoxyethane; DMF, N,N-dimethylformamide; DMSO, dimethylsulfoxide; Fmoc, 9-fluorenylmethoxycarbonyl; g, gram; h, hour; HATU, N-[(dimethylamino)-1H-1,2,3-triazolo-[4,5-b]pyridin-1-yl-methylene]-N-methylmethanaminium hexafluorophosphate N-oxide; mL, milliliter; NMM, N-methylmorpholine; NMP, N-methylpyrrolidinone; p-TsOH, para-toluenesulfonic acid; PyAOP, 7-azabenzotriazol-1-yl-oxytris(pyrrolidino) phosphonium hexafluorophosphate; PyBroP, bromo-tris-pyrrolidino-phosphonium hexafluorophosphate; rt, room temperature; TFA, trifluoroacetic acid; THF, tetrahydrofuran; w/w, weight per weight ratio.

Unless otherwise indicated, reactants and reagents are commercially available from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), Bachem (Philadelphia Pa. or Torrance Calif.); BDH Inc. (Toronto, Canada), Calbiochem (La Jolla Calif.), Eastman Organic Chemicals, Eastman Kodak Company (Rochester N.Y.), Fisher Scientific Co. (Pittsburgh Pa.), ICN Biomedicals, Inc. (Costa Mesa Calif.), Lancaster Synthesis (Windham N.H.), Maybridge Chemical Co. Ltd. (Cornwall U.K.), Novabiochem (see Calbiochem), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Example 1

Synthesis of {4-[(3S)-Allyloxycarbonylmethyl-(7S)-(9H-Fluoren-9-Ylmethoxycarbonylamino)-1,4-Dioxo-Hexahydro-Pyrrolo[1,2-A]Pyrazin-(2S)-Ylmethyl]-Phenyl}-Acetic Acid, 6

Figure 3:
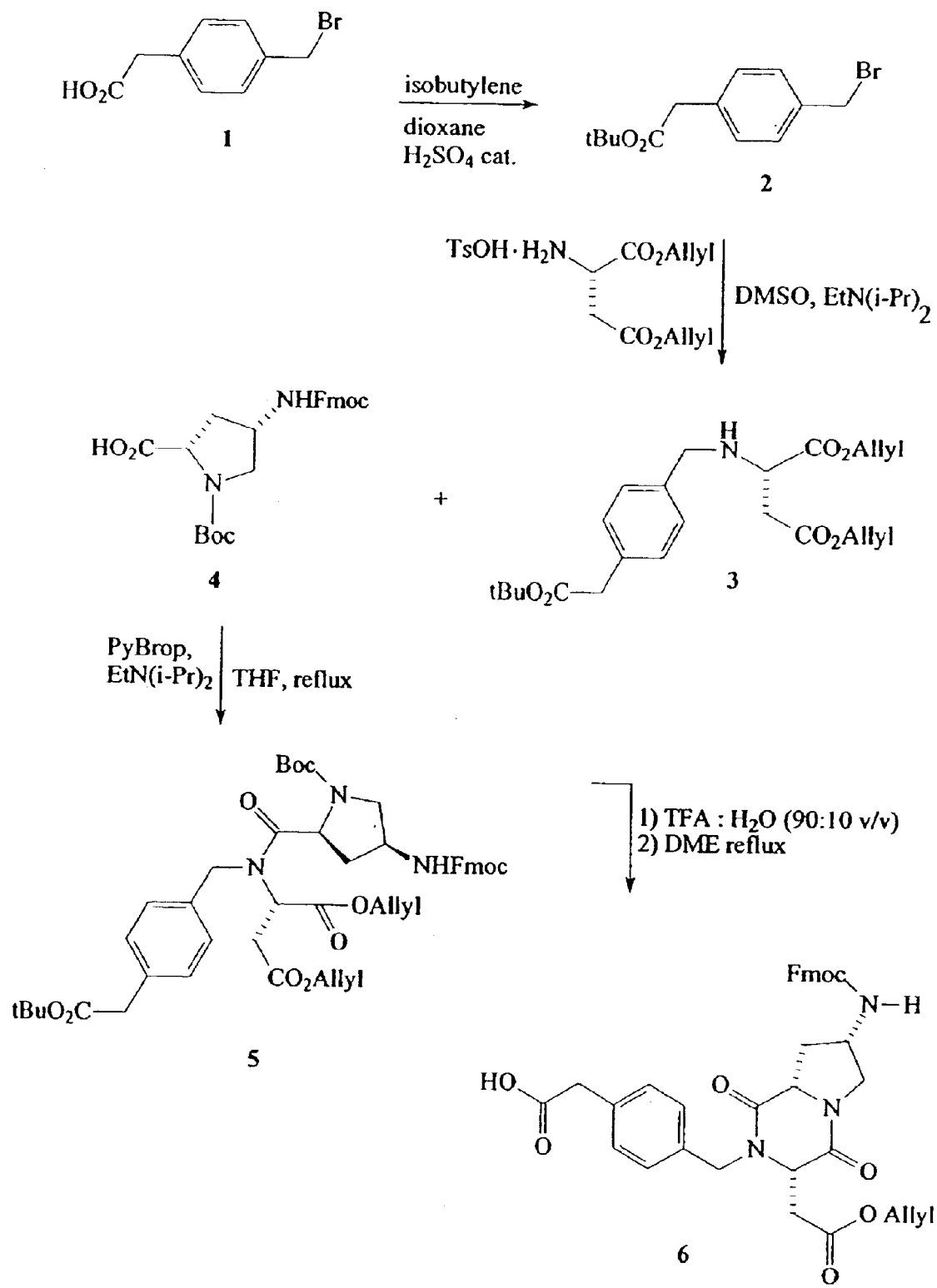
FIG. 3 illustrates a synthetic scheme for preparing a specific DKP compound 6 of the present invention.

FIG. 3 illustrates a solution-phase synthesis of a protected form of a bicyclic diketopiperazine (DKP) scaffold, 6, suitable for further elaboration to provide additional compounds of the present invention.

(2S)-(4-tert-Butoxycarbonylmethyl-benzylamino)-succinic acid diallyl ester, 3

A portion of isobutylene (bp −6.9° C., 100 mL at −78° C.) that was freshly condensed into a pre-marked flask immersed in a cold bath (−78° C. bath) was transferred to a cold (−78° C. bath) suspension of 4-bromomethylphenylacetic acid (22.5 g, 98.2 mmol), 1, in 1,4-dioxane (200 mL) in a thick-walled glass pressure-tube. Fuming sulfuric acid (36 N aqueous, 5 mL) was cooled to 0° C. (bath) and added dropwise with agitation to this suspension. (Caution: employ protective shielding and mix well during this addition to prevent localized warming and potentially hazardous boiling.) The reaction vessel was sealed and allowed to warm to rt with stirring. After 48 h, the resulting solution was cooled (0° C. bath), cautiously opened to the atmosphere, and allowed to slowly warm to rt over several hours with stirring. After evolution of the volatile components had subsided, aqueous workup (10% w/w aqueous NaHCO$_3$, diethyl ether, Na$_2$SO$_4$) of the solution afforded 2, (4-bromomethyl-phenyl)-acetic acid tert-butyl ester (18.2 g, 63.8 mmol, 65%), as a white amorphous solid: $^1$H NMR (300 MHz, CDCl$_3$) δ 7.35 (d, J=8.1 Hz, 2H), 7.24 (d, J=8.1 Hz, 2H), 4.48 (s, 2H), 3.52 (s, 2H), 1.43 (s, 9H).

A solution of 2 (15.0 g, 52.6 mmol) in DMSO (60 mL) was added, with stirring at rt, to a solution of the p-TsOH salt of L-aspartic acid diallyl ester (BaChem; 40.5 g, 105 mmol) in EtN(i-Pr)$_2$ (34.0 g, 263 mmol) and DMSO (120 mL) to afford a biphasic solution. After 24 h, aqueous work-up (H$_2$O, CH$_2$Cl$_2$, Na$_2$CO$_3$) of the biphasic solution afforded a crude yellow oil (30 g). Flash chromatography (gradient of hexanes to 4:1 hexanes/ethyl acetate) afforded 3 (18.0 g, 43.2 mmol, 82%) as a colorless oil: $^1$H NMR (300 MHz, CDCl$_3$) δ 7.27 (d, J=8.4 Hz, 2H), 7.20 (d, J=8.4 Hz, 2H), 5.98–5.82 (m, 2H), 5.36–5.20 (m, 4H), 4.63 (dt, J=5.7, 1.4 Hz, 2H), 4.58 (br d, J=5.7 Hz, 2H), 3.87 (d, J=13.2 Hz, 1H), 3.74–3.67 (m, 2H), 3.50 (s, 3H), 2.82–2.67 (AB m, 2H), 1.41 (s, 9H); $^{13}$C NMR (75 MHz, CDCl$_3$) δ 168.9, 166.6, 166.1, 133.6, 129.1, 127.4, 127.3, 124.7, 123.9, 114.2, 114.0, 76.2, 61.2, 60.9, 52.4, 47.1, 37.7, 33.5, 23.4.

(2S)-[[1-tert-Butoxycarbonyl-(4S)-(9H-fluoren-9-ylmethoxycarbonylamino)-pyrrolidine-(2S)-carbonyl]-(4-carboxymethyl-benzyl)-amino]-succinic acid diallyl ester, 5

To a solution of 4 (2S, 4S)-1-(tert-butoxycarbonyl)-4-amino-(9-fluorenylmethoxycarbonyl)-L-proline (14.4 g, 31.9 mmol, available from Neosystems Laboratoire, Peptide Dpt. Of Isochem SA, 75181 Paris cedex 04, France) in THF (100 mL) were consecutively added at rt: i) a solution of EtN(i-Pr)$_2$ (11.1 g, 85.8 mmol) in THF (100 mL); ii) neat PyBrop (Novabiochem, 17.2 g, 36.8 mmol); and iii) a solution of 3 (10.2 g, 24.5 mmol). The resulting suspension was warmed (65° C. bath) for 24 h then allowed to cool to rt and filtered through Celite. The yellow filtrate was concentrated in vacuo to afford a brown oil (30 g) which, after aqueous work-up (10% w/w aqueous citric acid, CH$_2$Cl$_2$, Na$_2$SO$_4$) and flash chromatography (gradient of 8:1 hexanes/ethyl acetate to 100% ethyl acetate), afforded 5 (12.0 g, 14.1 mmol, 58%) as a white crystalline solid: $^1$H NMR (300 MHz, CD$_3$OD) δ 7.76 (d, J=7.5 Hz, 2H), 7.61 (d, J=6.6 Hz, 2H), 7.47–7.12 (m, 8H), 6.00–5.70 (m, 2H), 5.28–5.07 (m, 4H), 4.84 (s, 2H), 4.79–4.15 (m, 7H), 3.77–3.70 (m, 1H), 3.51 (s, 2H), 3.45–3.05 (m, 2H), 2.72–2.56 (m, 2H), 1.46–1.43 (m, 9H); MS EI, 47 eV) m/z 890 (MK$^+$, 41), 874 (MNa$^+$, 100).

{4-[(3S)-Allyloxycarbonylmethyl-(7S)-(9H-fluoren-9-ylmethoxycarbonylamino)-1,4-dioxo-hexahydro-pyrrolo[1,2-a]pyrazin-(2S)-ylmethyl]-phenyl}-acetic acid, 6

A solution of 5 (19 g, 22 mmol) in H$_2$O/trifluoroacetic acid (10:90 v/v, 200 mL) was stirred at rt for 1 h. The solution was concentrated at rt in vacuo to afford a light brown oil which was diluted with 1,2-dimethoxyethane (250 mL) and refluxed for 30 min. The resulting solution was allowed to cool to rt then concentrated in vacuo to afford a viscous yellow foam which, after aqueous work-up (1 M aqueous HCl, ethyl acetate, MgSO$_4$) and flash chromatography (gradient of 1:1 hexanes/ethyl acetate to 99:1 ethyl acetate/acetic acid to 90:9:1 ethyl acetate/methanol/acetic acid), afforded 6 as a white amorphous solid (12 g, 19 mmol, 86%). $^1$H NMR (300 MHz, CD$_3$OD) δ 7.78 (d, J=7.5 Hz, 2H), 7.63 (d, J=7.5 Hz, 2H), 7.40–7.17 (m, 9H), 5.86–5.73 (m, 1H), 5.24–5.13 (m, 2H), 4.81 (d, J=15.9 Hz, 1H), 4.56 (d, J=15.9 Hz, 1H), 4.46–4.31 (m, 6H), 4.19 (t, J=6.6 Hz, 1H), 3.72–3.54 (m, 5H), 3.13–2.88 (m, 2H), 2.71–2.62 (m, 1H), 2.16 q, J=10.5 Hz, 1H). An analytical sample of 6 was obtained by crystallization (CH$_2$Cl$_2$/ethyl acetate): $^{13}$C NMR (75 MHz, d-6 DMSO) δ 169.8, 168.3, 164.3, 156.1, 144.1, 141.0, 135.1, 132.6, 129.8, 127.9, 127.3, 126.8, 125.3, 120.4, 118.1, 65.6, 64.7, 57.3, 55.8, 49.7, 48.1, 46.7, 45.5, 41.8, 34.3, 33.0, (21.6); MS (EI, 34 eV) m/z 1297 (2M$^+$Na$^+$, 24), 660 (MNa$^+$, 100), 638 (M$^+$, 20).

Example 2

Synthesis of Quinoline-3-Carboxylic Acid [2-(4-Carbamoylmethyl-Benzyl)-(3S)-Dipentylcarbamoyl Methyl-1,4-Dioxo-Octahydro-Pyrrolo[1,2-A] Pyrazin-(7S)-yl]-amide, 20

This Example illustrates the synthesis of a representative DKP of this invention, 20, from scaffold 6 via General Method A. FIGS. 3A and 3B show the synthetic route employed.

General Method A:

Parallel synthesis in solution with purification. "Parallel synthesis" refers to the synthesis of multiple DKPs in the format of a single DKP per reaction vessel. Reaction vessel (RV) or "well" refers to a borosilicate glass or Teflon vessel with sintered glass frit or polypropylene porous filter, respectively.

((7S)-(9H-Fluoren-9-ylmethoxycarbonylamino)-1,4-dioxo-2-{4-[(2,4,6-trimethoxy-benzylcarbamoyl)-methyl]-benzyl}-octahydro-pyrrolo[1,2-a]pyrazin-(3S)-yl)-acetic acid allyl ester, 15

Neat 2,4,6-trimethoxybenzylamine hydrochloride (320 mg, 1.38 mmol) was added to a solution of 6 (800 mg, 1.25 mmol), NMM (600 mg, 5.94 mmol) and HATU (620 mg, 1.63 mmol) in CH$_2$Cl$_2$ (20 mL) and the resulting solution was stirred at rt for 2 h. Aqueous work-up (2% aqueous HCl, CH$_2$Cl$_2$, Na$_2$SO$_4$) and concentration in vacuo afforded a light brown oil (1.2 g) which after flash chromatography (gradient of 2:1 hexanes/ethyl acetate to ethyl acetate) afforded 15 as a white solid (790 mg, 0.967 mmol, 77%). $^1$H NMR (300 MHz, CD$_3$CN) δ 7.82–7.10 (m), 6.54–6.50 (m), 6.27–6.10 (m), 5.84–5.70 (m), 5.25–5.14 (m), 4.84–4.78 (m), 4.47–4.10 (m), 3.77 (s, 2H), 3.58 (m), 3.44 (s, 2H), 3.09–2.80 (m), 2.20–2.00 (m); $^{13}$C NMR (75 MHz, CD$_3$CN) δ 170.3, 166.7, 163.9, 160.9, 159.2, 155.9, 143.8, 141.3, 135.0, 134.5, 131.2, 130.1, 129.7, 127.9, 127.7, 127.1, 125.0, 119.9, 119.2, 106.0, 90.4, 66.7, 65.9, 57.6, 56.0, 55.5, 55.2, 52.4, 52.4, 48.4, 47.0, 43.0, 36.0, 34.1, 32.6.

(1,4-Dioxo-(7S)-[(quinoline-3-carbonyl)-amino]-2-{4-[(2,4,6-trimethoxy-benzylcarbamoyl)-methyl ]-benzyl}-octahydro-pyrrolo[1,2-a]pyrazin-(3S)-yl)-acetic acid allyl ester, 21

A solution of 15 (122 mg, 0.149 mmol) in CH$_3$CN (3.0 mL) was diluted with piperidine (1.0 mL). The resulting solution was stirred at rt for 2 h. Aqueous work-up (pH 5 phosphate buffer, ethyl acetate, Na$_2$SO$_4$) and concentration in vacuo afforded a yellow oil (125 mg) which was recrystallized (CH$_2$Cl$_2$) to afford a white solid (85 mg, 0.14 mmol, 94%). Without further purification, this primary amine intermediate, i.e., ((7S)-amino-1,4-dioxo-2-{4-[(2,4,6-trimethoxy-benzylcarbamoyl)-methyl]-benzyl}-octahydro-pyrrolo[1,2-a]pyrazin-(3S)-yl)-acetic acid allyl ester, was diluted with CH$_2$Cl$_2$ (1.0 mL) followed by a solution of 3-quinoline carboxylic acid (29 mg, 0.17 mmol), NMM (38 mg, 0.38 mmol) and PyAOP (0.17 mmol) in CH$_2$Cl$_2$ (1.0 mL). The resulting solution was stirred at rt for 90 min. Aqueous work-up (10% w/w aqueous NaHCO3, ethyl acetate, Na$_2$SO$_4$) and concentration in vacuo afforded a light brown oil (188 mg) which after flash chromatography (2% triethylamine in ethyl acetate) afforded 21 as a white solid (60 mg, 0.080 mmol, 53%). $^1$H NMR (300 MHz, CDCl$_3$) δ 9.28 (d, J=1.5 Hz, 1H), 8.63 (s, 1H), 8.14 (d, J=8.4 Hz, 1H), 7.85–7.74 (m, 2H), 7.58 (dd, J=7.8, 7.2 Hz, 1H), 7.14 (s, 4H), 6.05 (s, 2H), 5.90 (br s, 1H), 5.68–5.55 (m, 1H), 5.11–4.90 (m, 4H), 4.42–4.20 (m, 7H), 3.89–3.69 (m, 11H), 3.51–3.42 (m, 3H), 3.25 (dd, J=17.4, 2.7 Hz, 1H), 3.02–2.89 (m, 2H), 2.53–2.45 (m, 1H); $^{13}$C NMR (75 MHz, d-6 CDCl$_3$) δ 170.9, 169.8, 166.7, 165.2, 163.9, 160.9, 159.2, 148.0, 136.9, 135.3, 134.2, 131.7, 130.9, 130.1, 128.8, 127.7, 127.9, 127.7, 127.0, 119.0, 106.3, 90.4, 83.5, 66.2, 57.3, 56.0, 55.6, 55.2, 52.6, 47.4, 46.8, 43.2, 36.3, 34.4, 32.5; MS (EI, 20 eV) m/z 772 (MNa$^+$, 100), 750 (M$^+$, 60).

(1,4-Dioxo-(7S)-[(quinoline-3-carbonyl)-amino]-2-{4-[(2,4,6-trimethoxy-benzylcarbamoyl)-methyl]-benzyl}-octahydro-pyrrolo[1,2-a]pyrazin-(3S)-yl)-acetic acid methyl ester, 18

Treatment of 21 by column chromatography with methanol as co-eluent (SiO$_2$ with a gradient of ethyl acetate to 9:1 v/v ethyl acetate/methanol) provided extensive transesterification, during the elution, which afforded 18 as a white amorphous solid.

Quinoline-3-carboxylic acid ((3S)-dipentylcarbamoylmethyl-1,4-dioxo-2-{4-[(2,4,6-trimethoxy-benzylcarbamoyl)-methyl]-benzyl}-octahydro-pyrrolo[1,2-a]pyrazin-(7S)-yl)-amide 22

Neat potassium trimethylsiloxide (68 mg, 0.52 mmol) was added to a solution of 18 (130 mg, 0.174 mmol) in $CH_2Cl_2$ (2 mL). After 15 min, the resulting suspension was diluted with diethyl ether and the voluminous precipitant was collected by filtration, washed with additional portions of diethyl ether and dried to afford the intermediate carboxylate salt 23 (1,4-dioxo-(7S)-[(quinoline-3-carbonyl)-amino]-2-{4-[(2,4,6-trimethoxy-benzylcarbamoyl)-methyl]-benzyl}-octahydro-pyrrolo[1,2-a]pyrazin-(3S)-yl)-acetic acid trimethoxy benzylamide as a white solid (130 mg).

Without further purification, this material was diluted with NMP (2.0 mL) followed by a solution of N,N-di(n-pentyl)amine (41 mg, 0.26 mmol), NMM (53 mg, 0.52 mmol) in NMP (1.0 mL) and a solution of HATU (99 mg, 0.26 mmol) in NMP (1.0 mL). The resulting solution was stirred at rt for 5 h. Aqueous work-up (pH 5 phosphate buffer, ethyl acetate, $Na_2SO_4$) and concentration in vacuo afforded a light brown oil (180 mg) which after flash chromatography (gradient of ethyl acetate to 2% triethylamine in 9:1 ethyl acetate/methanol) afforded 22 as a white amorphous solid (110 mg, 0.130 mmol, 75%). $^1H$ NMR (300 MHz, $CDCl_3$) δ (~2:1 mixture of amide rotational isomers at rt; complex, not completely analyzed): 9.38 (d, J=2.1 Hz, ⅔H), 9.23 (d, J=2.4 Hz, ⅓H), 8.76 (br s, ⅔H), 8.66 (br s, ⅓H), 8.14–8.09 (AB dd, J=8.7, 8.4 Hz, 2H), 7.98–7.75 (m, 4H), 7.62–7.54 (AB dd, J=7.8, 7.5 Hz, 2H), 7.15 (s, 2H), 7.09–7.00 (AB dd, J=8.4, 8.1 Hz, 2H), 6.21–5.93 (m, 3H), 4.93–2.27 (m,), 1.78 (m, 1H); MS (EI, 15 eV) m/z 887 ($MK^+$, 30), 871 ($MNa^+$, 40), 849 (100).

Quinoline-3-carboxylic Acid [2-(4-carbamoylmethyl-benzyl)-(3S)-dipentylcarbamoyl methyl-1,4-dioxo-octahydro-pyrrolo[1,2-a]pyrazin-(7S)-yl]-amide, 20

A solution of 22 (90 mg, 0.11 mmol) in TFA/water (9:1 v/v, 5.0 mL) was warmed (80° C. bath) for 1h. The resulting deep violet solution was concentrated in vacuo and the resulting solid was purified by column chromatography (gradient of ethyl acetate to 9:1 ethyl acetate/methanol) to afford 20 as a white solid (51 mg, 0.076 mmol, 69%). $^1H$ NMR (300 MHz, $CDCl_3$ with 10% v/v $CD_3OD$) δ 9.43 (d, J=1.8 Hz, 1H), 9.17 (d, J=1.2 Hz, 1H), 8.82 (d, J=8.4 Hz, 1H), 8.48 (d, J=8.4 Hz, 1H), 8.11–8.03 (m, 2H), 7.86 (AB dd, J=7.8, 7.5 Hz, 1H), 7.20 (d, J=8.1 Hz, 2H), 7.13 (d, J=8.1 Hz, 2H), 6.90 (br s, 1H), 6.45 (br s, 1H), 4.89 (d, J=15.6 Hz, 1H), 4.44–4.29 (m, 4H), 3.53 (s, 2H), 3.47–3.40 (m, 1H), 3.23–2.82 (m, 8H), 2.60–2.56 (m, 1H), 1.55–0.75 (m, 15H), 0.63 (t, J=7.2 Hz, 3H); $^{13}C$ NMR (75 MHz, $CDCl_3$ with 10% v/v $CD_3OD$) δ 176.0, 169.1, 167.1, 165.7, 162.6, 144.1, 143.6, 141.0, 135.4, 135.2, 133.9, 130.2, 130.1, 129.5, 128.4, 128.0, 127.7, 123.2, 70.2, 57.8, 56.9, 52.5, 48.1, 47.3, 46.2, 41.9, 35.4, 32.9, 28.8, 28.6, 28.0, 26.8, 22.1, 21.9, 13.7, 13.5; MS (API, 30 eV) m/z 669 ($MH^+$, 100).

Example 3

Solid-Phase Synthesis of Representative Bicyclic Diketopiperazines

Figure 6:
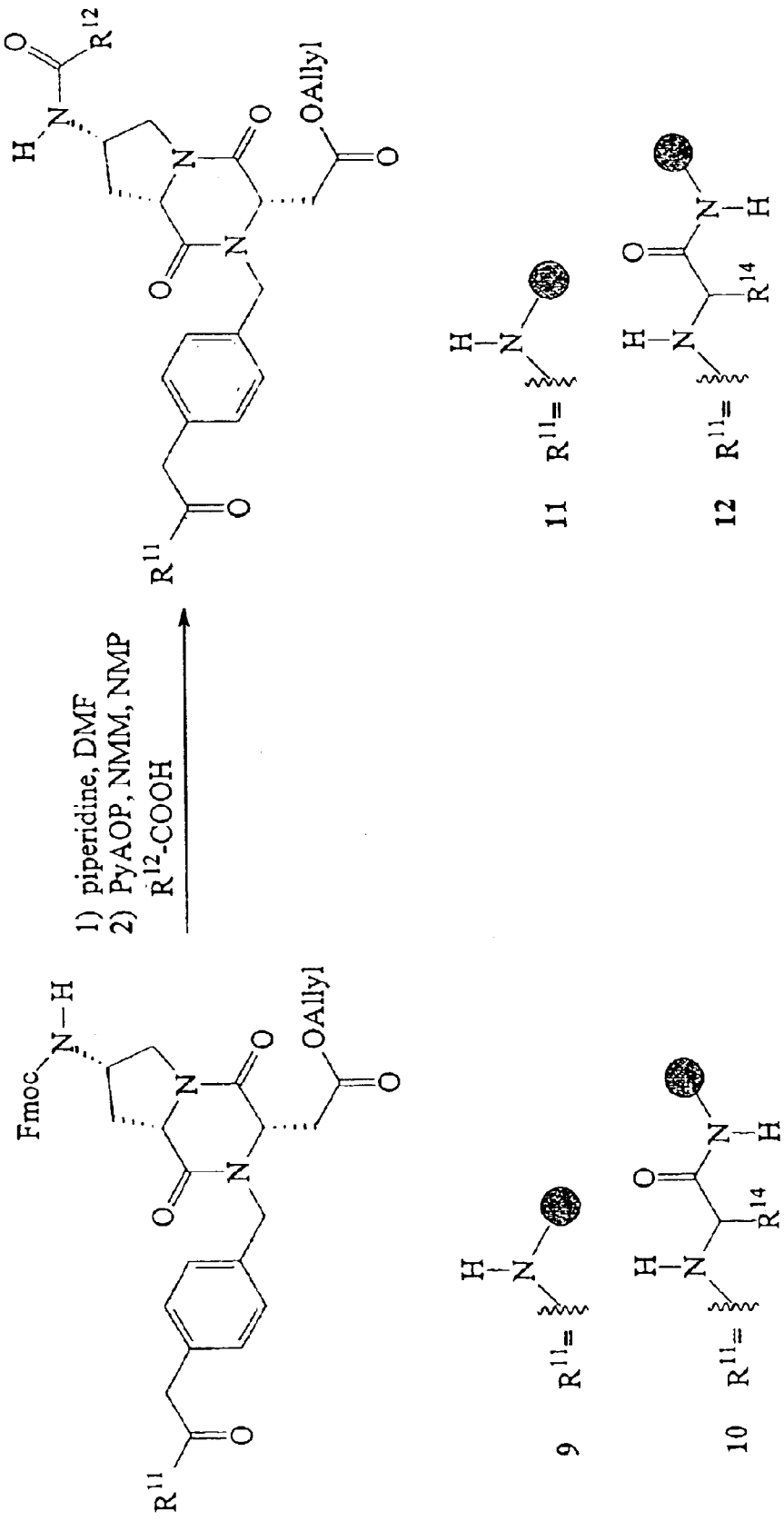
Figure 7:
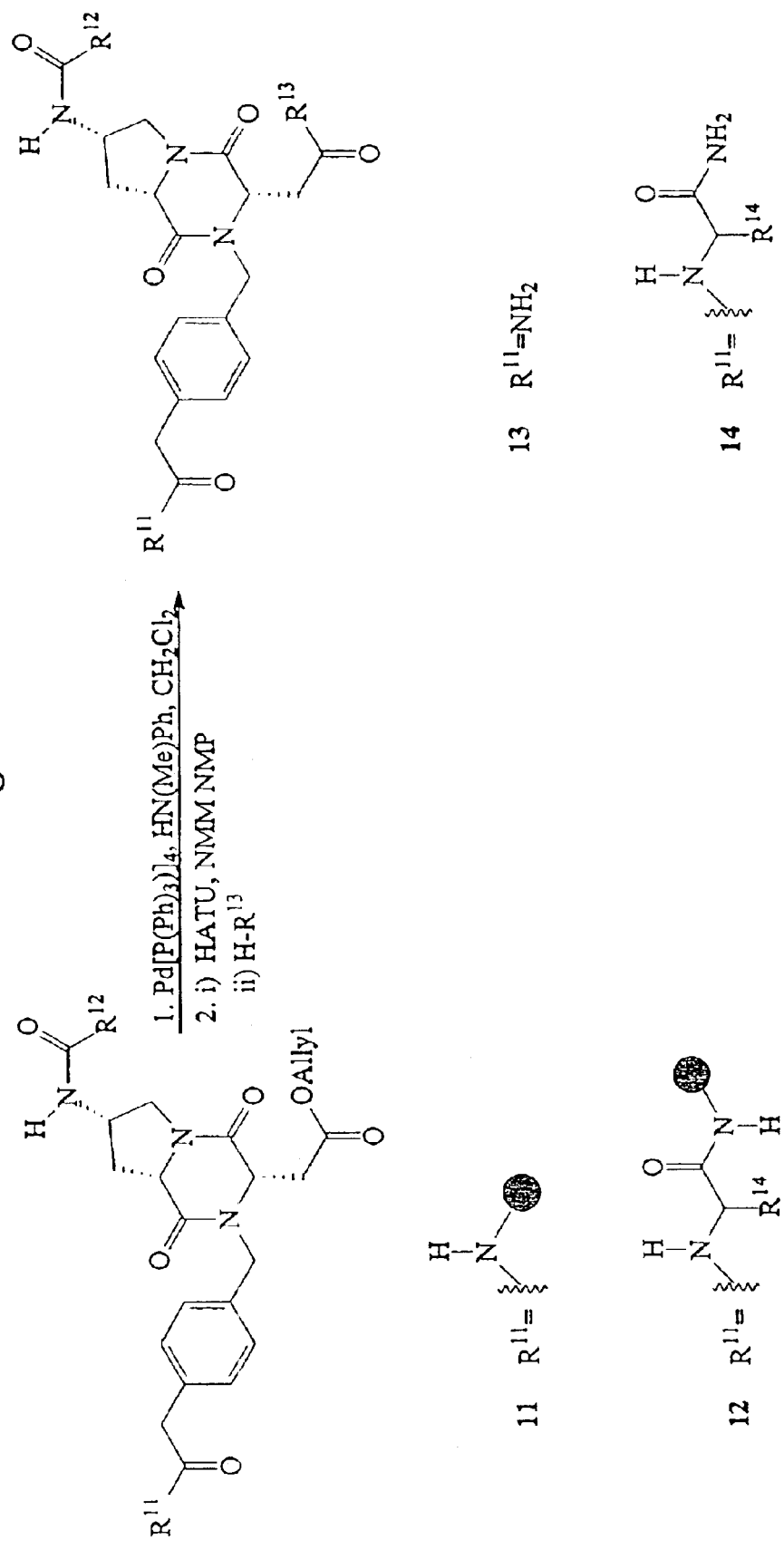

This Example illustrates the solid phase synthesis of representative bicyclic diketopiperazines. Solid phase synthesis can be used to prepare individual DKP compounds or libraries of DKP compounds. Libraries may be produced using either parallel or combinatorial methods, where each of these methods is described below. FIG. 2 (as described previously) summarizes the synthetic route employed, while FIGS. 5, 6 and 7 provide more details regarding the steps summarized in FIG. 2.

Solid-Supported Synthesis Protocols for Preparation of Bicyclic Diketopiperazines:

Bicyclic diketopiperazine libraries were synthesized by one or more of the following three (B-D) protocols: B) parallel synthesis on solid-support with purification; C) parallel synthesis on solid-support without purification; D) combinatorial synthesis on solid-support without purification. In the following description of library preparation, reaction vessel (RV) or "well" refers to a borosilicate glass or Teflon vessel with sintered glass frit or polypropylene porous filter, respectively. "Empty RV's" means to drain the solvent through the frit or filter, leaving the solid phase in the well. Agitation and filtration were accomplished using an upward positive nitrogen pressure through a porous filter or orbital shaking motion. "Wash" means add solvent, agitate ca. 30 sec. then filter and repeat (x3). Methods B–D may employ robotic workstations.

During the development of these reaction conditions and as subsequent, periodic checks of automated production runs, one or more aliquots of resin were typically tested after each synthetic transformation on solid support. Also, subsequent cleavages, after individual reaction steps, typically afforded intermediates (and final products) in 90–100% yield, after chromatography, based on the theoretical loading of the commercial resin.

Reagents:

TentaGel SRAM Fmoc resin was purchased from NovaBiochem (load=0.26 mol/g). Reagent 1=NMP in DCM (3:1 v/v); Reagent 2=piperidine (1:4 v/v in NMP); Reagents 3–14=set of twelve racemic N-Fmoc amino acids having structures Fmoc-NH—CH($R^{14}$)—COOH where $R^{14}$ is defined in Table A, twelve solutions each of a single racemic N-Fmoc amino acid (0.25 M "a, b, c . . . through l" in NMP); Reagent 15=0.50 M PyAOP and 1.25 M NMM (in NMP); Reagent 16=psuedo-orthogonally protected scaffold 6 (0.25 M in NMP) where $R^{11}$ =OH; Reagent 17–28=set of twelve carboxylic acids having structures $R^{12}$—COOH where $R^{12}$ is defined in Table B as one of twelve solutions each of a single carboxylic acid (0.25 M "aa, bb, cc . . . through ll" in NMP); Reagent 29=N-methylaniline (0.25 M in $CHCl_3$); Reagent 30=$Pd(PPh_3)_4$ (0.025 M in $CHCl_3$); Reagent 31=diethylthiocarbamate salt and DIEA (0.02 and 0.04 M respectively in NMP); Reagent 32–43=set of twelve amines having the structure $R^{13}$—$NH_2$ where $R^{13}$ is defined in Table C, and each solution is one of twelve individual amines (0.25 M "aaa, bbb, ccc . . . through lll" in NMP); Reagent 44=0.50 M HATU and 1.25 M NMM (in NMP); Reagent 45=$H_2O$ (1:10 v/v in trifluoroacetic acid).

TABLE A*

$R^{14}$ DIVERSITY SET

| a | g |
|---|---|

TABLE A*-continued

$R^{14}$ DIVERSITY SET

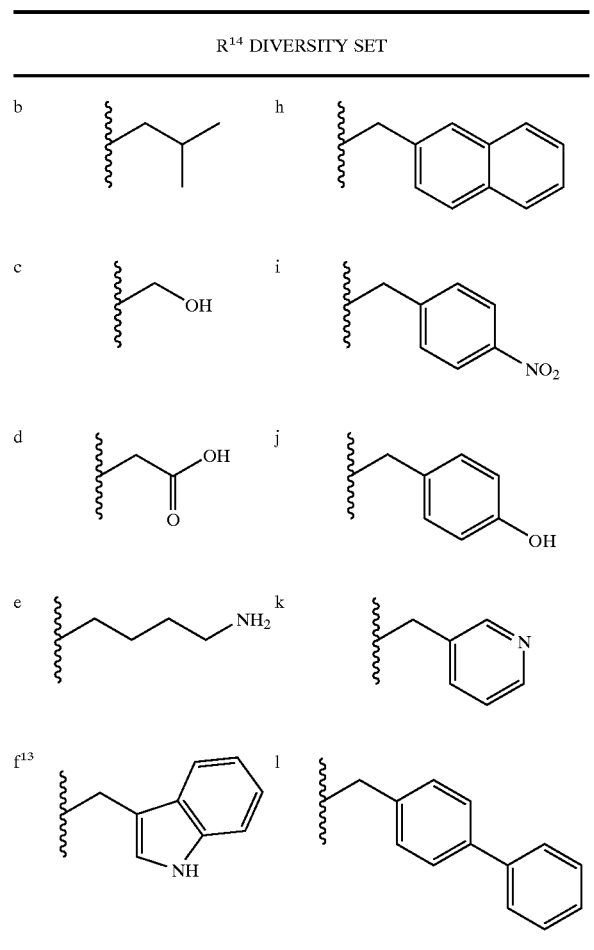

*primary or secondary amines, and carboxylic acids, were protected as t-butylcarbamates and t-butyl esters, respectively, throughout synthesis until final acid promoted cleavage from the solid support, with concomitant deprotection.

TABLE B*

$R^{12}$ DIVERSITY SET

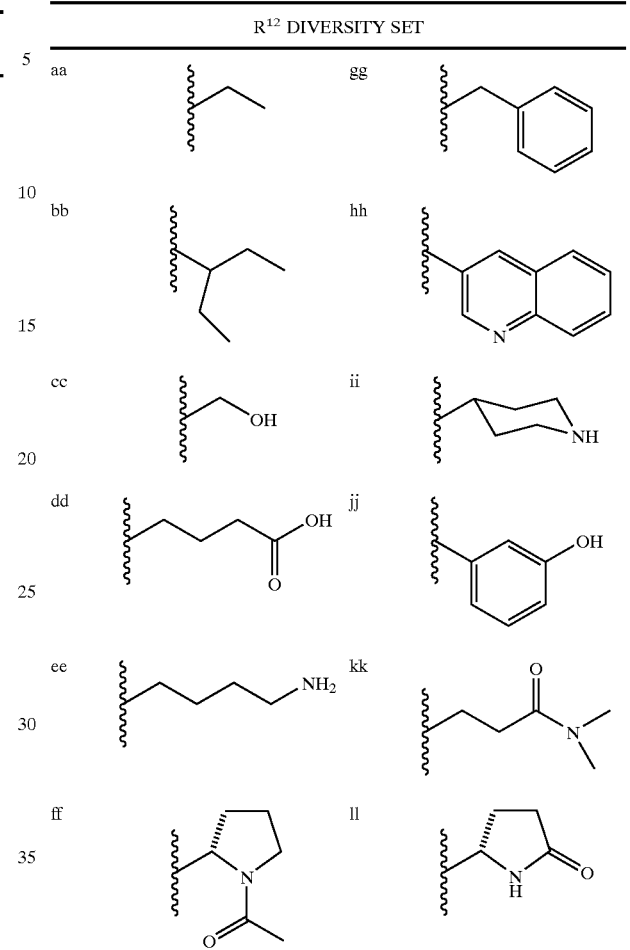

*primary or secondary amines, and carboxylic acids, were protected as t-butylcarbamates and t-butyl esters, respectively, throughout synthesis until final acid promoted cleavage from the solid support, with concomitant deprotection.

TABLE C*

$R^{13}$ DIVERSITY SET

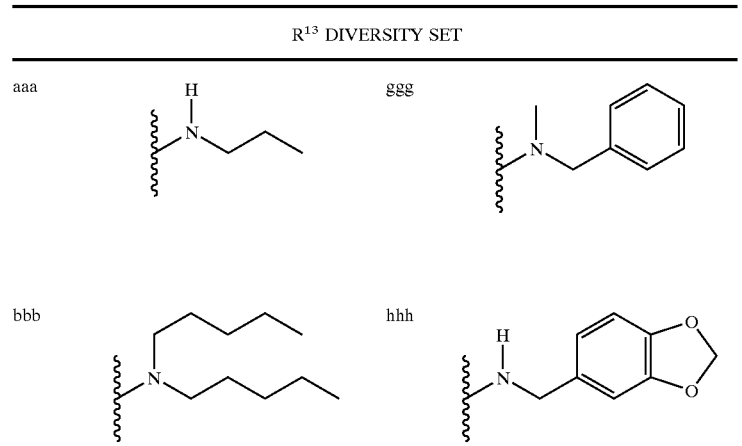

TABLE C*-continued

R¹³ DIVERSITY SET ccc: [structure - N-H-cyclohexyl-CH2 with cyclohexane-COOH]
ddd: [structure - N-H-CH2CH2-C(=O)-OH]
eee: [structure - N-H-(CH2)4-NH2]
fff: [structure - pyrrolidine with C(=O)N(CH3)2]
iii: [structure - piperazine N-methyl]
jjj: [structure - N-H-CH2CH2-phenyl-OH]
kkk: [structure - N-H-CH2CH2-NH-C(=O)CH3]
lll: [structure - N-H-piperidine-N-C(=O)-O-ethyl]

*primary or secondary amines, and carboxylic acids, were protected as t-butylcarbamates and t-butyl esters, respectively, throughout synthesis until final acid promoted cleavage from the solid support, with concomitant deprotection.

FIG. 5 illustrates the preparation of DKP precursors of general structures 9 and 10 on solid support, according to steps 1–6 below.

1. Equally divide dry resin into at least twelve RVs (0.26 meq/g; 125 mg total resin per well); then dispense DCM (1.0 mL per well) and agitate for 5 min. Empty RV's, and wash with NMP (3×1.0 mL per well).

2. Perform the following steps twice: Dispense Reagent 2 (1.0 mL per well); then agitate for 10 min; then empty RV's; then wash with NMP (3×1.0 mL per well).

3. Omit this step and go to step 4 for the preparation of 9, but follow this step for the preparation of 10, and then go to step 4. Dispense NMP (0.013 mL per well); then dispense Reagents 3–14 (0.20 mL of one of these reagents per well; 3.0 eq N-Fmoc amino acid). For example, to one RV, dispense Reagent 8 (0.20 mL per well; 1.5 eq "f", racemic N-Fmoc, N-Boc tryptophan); 012) dispense Reagent 15 (0.10 mL per well; 3.0 eq PyAOP and 7.6 eq NMM); 013) agitate for 90 min; 014) empty RV's; 015) wash with NMP (3×1.0 mL per well).

4. Perform the following steps twice: Dispense Reagent 2 (1.0 mL per well), then agitate for 10 min; then empty RV's; then wash with NMP (3×1.0 mL per well).

5. Perform the following steps twice: Dispense NMP (0.43 mL per well); then dispense Reagent 16 (0.133 mL per well; 1.0 eq 6); then dispense Reagent 15 (0.067 mL per well; 1.0 eq PyAOP and 2.5 eq NMM); then agitate for 90 min; then empty RV's; then wash with NMP (3×1.0 mL per well).

6. For Method D only: Combine resin from several RVs above; then redivide resin (gravimetrically as a dry powder or volumetrically as an isopycnic slurry suspended in solvent) into several equal parts (for example, 0.26 meq/g; 0.065 meq/well); then empty RV's; and then wash with NMP (3×2.0 mL per well).

FIG. 6 illustrates the synthesis of derivatives at the R¹² diversity position, according to steps 7–9 below.

7. Dispense Reagent 2 (1.0 mL per well); then agitate for 10 min; then empty RV's; and then wash with NMP (3×1.0 mL per well).

8. Dispense NMP (0.33 mL per well); then dispense Reagents 17–28 (0.20 mL of one of these reagents per well; 3.0 eq carboxylic acid). For example, to one RV dispense Reagent 24 (0.20 mL per well; 1.5 eq "hh", quinoline carboxylic acid); then dispense Reagent 15 (0.10 mL per well; 1.5 eq PyAOP and 3.8 eq NMM); then agitate for 90 min; then empty RV's; and then wash with NMP (3×1.0 mL per well).

9. For Method D only: Combine resin from several RVs; then redivide resin (gravimetrically as a dry powder or volumetrically as an isopycnic slurry suspended in solvent) into several equal parts (for example, 0.26 meq/g; 0.065 meq/well); then empty RV's; and then wash with NMP (3×2.0 mL per well).

FIG. 7 illustrates the synthesis of derivatives at the R¹³ diversity position, according to steps 10–13 below.

10. Wash with $CHCl_3$ (3×1.0 mL per well); then dispense Reagent 29 (0.275 mL per well; 2.1 eq NMA); then dispense Reagent 30 (0.5 mL per well; 0.38 eq Pd cat.); then agitate for 60 min (caution: minimize solvent evaporation); then empty RV's; and then wash with $CHCl_3$ (3×1.0 mL per well).

11. Dispense Reagent 31 (3×1.0 mL per well); then agitate for 10 min; and then empty RV's.

12. Wash resin with NMP (3×1.0 mL per well); then dispense NMP (0.32 mL per well); then dispense Reagent 44 (0.10 mL per well; 1.5 eq HATU and 3.8 eq NMM); then dispense Reagents 32–43 (0.20 mL of one of these reagents per well; 3.0 eq amine). For example, to one RV dispense Reagent 33 (0.20 mL per well; 1.5 eq "bbb", N,N-dipentylamine); then agitate for 90 min; then empty RV's; and then wash resin with NMP (3×1.0 mL per well).

13. Wash resin with NMP (3×1.0 mL per well); then wash with DCM (3×1.0 mL per well); then wash with MeOH (3×1.0 mL per well); then wash with DCM (3×1.0 mL per well); then dispense Reagent 45 (1.0 mL per well); then agitate for 45 min; then collect filtrate (i.e., empty RV's); then concentrate filtrate in vacuo; then dissolve residue in AcOH (0.50 mL per well) and dilute with toluene (0.50 mL per well) then concentrate in vacuo; then treat residue with toluene (1×1.0 mL per well) and concentrate in vacuo.

General Methods B, C, and D:

Method B

Figure 4A:
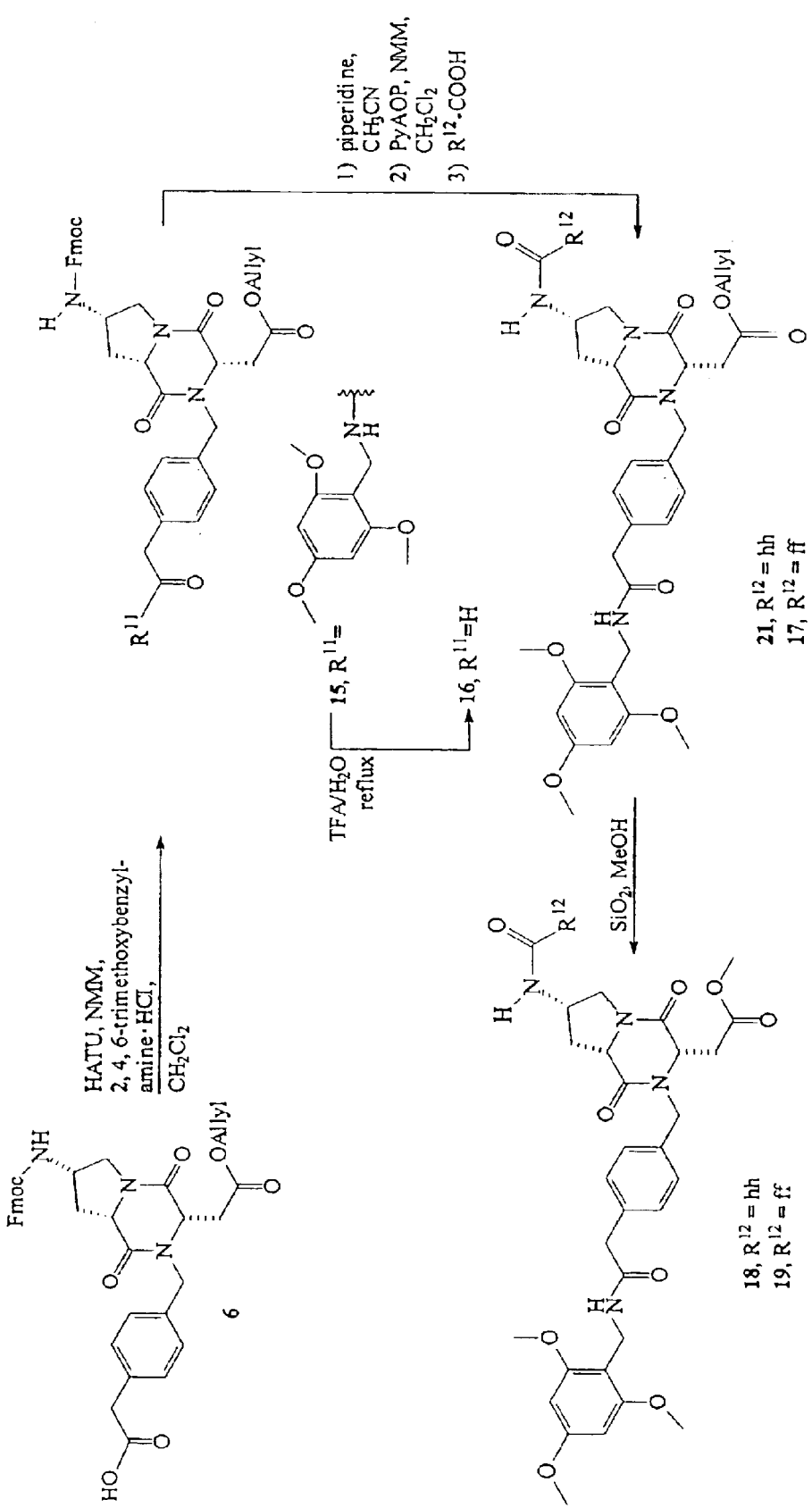
FIGS. 4A and 4B illustrate synthetic methodology whereby DKP compound 6 may be elaborated to additional DKP compounds of the present invention.
Figure 4B:
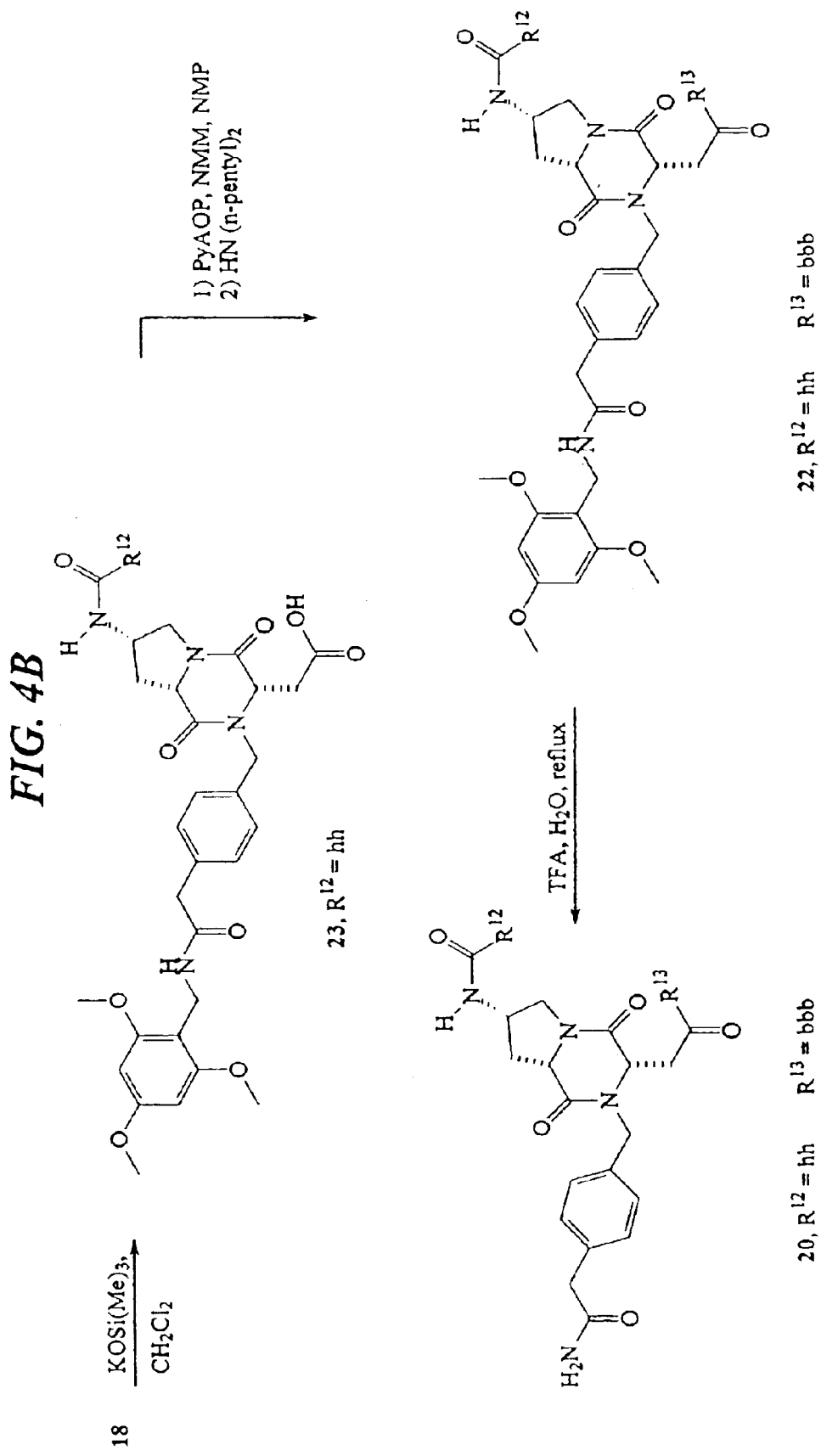

Samples were purified by flash column chromatography (SiO$_2$ w/EtOAc/MeOH eluents with either Et$_3$N or AcOH as co-eluent) and/or crystallization. Yield determination and spectral characterization was performed ($^1$H NMR, $^{13}$C NMR, MS). Typically, products were afforded as solids in 80–95% of theoretical yield based on initial load of the resin. For example, compound 20 was synthesized by Method B on a solid-support and purified by column chromatography (gradient of ethyl acetate to 9:1 ethyl acetate/methanol) to afford 20 as a white solid (98% overall yield based on theoretical load). This material corresponded ($^1$H NMR, $^{13}$C NMR and MS) to the same product that was prepared via a non-polymer supported synthesis involving well-characterized intermediates (see Example 1 and FIGS. 4A and 4B).

Method C

Acquired mass spectra on all samples. Acquired $^1$H NMR, weight and TLC on a subset of samples and compared these with the corresponding data for the authentic compounds that were prepared by method of Example 1 or Method B, previously. Evidence for product formation was based the appearance of a parent ion by MS (+APCI or −APCI) with intensity >25% of the base peak as well as qualitative comparison of 1H NMR, TLC and product weight for selected samples relative to authentic material prepared via Method A or B. Crude products were afforded in 90–100% of theoretical mass recovery (based on load estimation of the starting resin) and underwent biological assay without further purification.

Method D

Acquired mass spectra on all samples. Acquired $^1$H NMR, weight and TLC on a subset of samples and compared these with the corresponding data for authentic individual components that were prepared by Method A or B, previously. Evidence for product formation was based the appearance of a parent ion by MS (+APCI or −APCI) with intensity >25% of the base peak. Additionally, 14% of the library mixtures were examined by $^1$H NMR and all were found to display acceptable, characteristic $^1$H NMR resonances for the components in the crude mixture based on comparison to authentic reference spectra, of corresponding purified compounds, that were prepared via Method A or B. Crude products were afforded in 90–100% of theoretical mass recovery (based on load estimation of the starting resin) and underwent biological assay without further purification.

Example 4

Biological Activities of Representative Bicyclic Diketopiperazines

This example illustrates the ability of representative bicyclic diketopiperazines to function as inhibitors of TNF-α-induced apoptosis, TNF-α-induced expression of NFK-B, binding of TNF-α to TNFR, and binding of IL-8 or GRO-α to CXCR1 or CXCR2. The diketopiperazines were synthesized by the general methods disclosed herein. General assay procedures are given below, and data obtained from the procedures is set forth in TABLE D.

CXCR1:

This assay is a radioligand binding assay in human recombinant CHO cells with $^{125}$I labeled IL-8 as ligand as described in The Journal of Biological Chemistry (Ahuja, S. K.; Murphy, P. M;. *J. Biol. Chem.* 1996, 271, 20545). This assay was performed by Panlabs Taiwan, Ltd. In Table D, a compound showed activity in this assay when "I" appears in the column titled Biological Activity. The extent of activity is indicated by the letter following "I", where A refers to >50% inhibition at 20 μM, B refers to 40–50% inhibition at 20 μM, C refers to 30–40% inhibition at 20 μM, D refers to 20–30% inhibition at 20 μM, and E refers to 10–20% inhibition at 20 μM.

CXCR2:

This assay is a radioligand binding assay in human recombinant CHO cells with $^{125}$I labeled IL-8 as ligand as described in The Journal of Biological Chemistry (Ahuja, S. K.; Murphy, P. M;. *J. Biol. Chem.* 1996, 271, 20545). This assay was performed by Panlabs Taiwan, Ltd. In Table D, a compound showed activity in this assay when "II" appears in the column titled Biological Activity. The extent of activity is indicated by the letter following "II", where A refers to >50% inhibition at 20 μM, B refers to 40–50% inhibition at 20 μM, C refers to 30–40% inhibition at 20 μM, D refers to 20–30% inhibition at 20 μM, and E refers to 10–20% inhibition at 20 μM.

NFK-B:

A549 cells were stably transfected with an E-selectin promoter containing three NFK-B binding sites driving luciferase expression. For the assay, 5×10$^4$ cells were incubated in 96 well round bottom plates overnight in 100 μL of 10% FBS/RPMI medium at 37° C. in a 5% CO$_2$ atmosphere. The following morning the medium was removed and 90 μL of a 1% DMSO solution of compound solution was added and the plates incubated for 1 hour. 10 μL of TNF-αwas added at its EC$_{50}$ (normally 6 ng/mL) to each well and the plate incubated for 5 hours. 100 μL of luciferase buffer was added, and after 10 minutes luminescence was read on a Wallac Victor luminometer. In Table D, a compound showed activity in this assay when "IV" appears in the column titled Biological Activity. The extent of activity is indicated by the letter following "IV", where A refers to >50% inhibition at 20 μM, B refers to 40–50% inhibition at 20 μM, C refers to 30–40% inhibition at 20 μM, D refers to 20–30% inhibition at 20 μM, and E refers to 10–20% inhibition at 20 μM.

Apoptosis:

The protocol used for determining inhibition of apoptosis in A549 cells was adopted from a system previously described (K. Last-Barney et al, J. of Immunology, 1988, 141, 527–530). Briefly, 10$^5$ cells in 200 μL 10% FBS/RPMI antibiotic containing culture medium were plated into 96 well round bottom culture plates and allowed to adhere for 6 hours at 37° C. in a 5% CO$_2$ atmosphere. The media was removed and 100 μL of RPMI+1 μg/mL actinomycin-D was added to each well, followed by 100 μL of 20 μM solution of compound in 1% DMSO. This was incubated for 1 hour. TNF-α was added at its EC$_{50}$ (normally 1 ng/mL) and the plates incubated for 18 hours. The media was aspirated from the plates and 100 µL of 0.5% crystal violet in 20% methanol was added. After 10 minutes the plates were rinsed with water to remove excess stain, air dried, and read on a Spectramax spectrophotometer at a wavelength of 590 nm. In Table D, a compound showed activity in this assay when "III" appears in the column titled Biological Activity. The extent of activity is indicated by the letter following "III", where A refers to >50% inhibition at 20 µM, B refers to 40–50% inhibition at 20 µM, C refers to 30–40% inhibition at 20 µM, D refers to 20–30% inhibition at 20 µM, and E refers to 10–20% inhibition at 20 µM.

TNFR ($R^1$ and $R^2$, nonselective):

This assay is a radioligand binding assay in human U-937 cells with $^{125}I$ labeled TNF alpha as ligand as described in The *Journal of Biological Chemistry* (Baglioni C. et al. *J. Biol. Chem.* 1985, 260, 13395). This assay was performed by Panlabs Taiwan, Ltd., catalogue # 286510. None of the DKP compounds displayed significant activity in this assay.

Table D reports biological activity for DKP compounds of the structure:

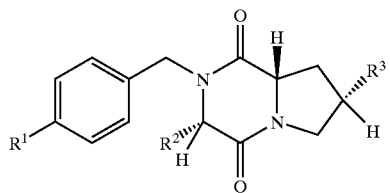

TABLE D

| $R^1$ | $R^2$ | $R^3$ | Biological Activity |
|---|---|---|---|
| (2,4,6-trimethoxybenzyl)-N-CH2-X1 | X2-CH(-)-CH2-COOH | X3-NH-C(O)-O-CH2-fluorenyl | IIA $IC_{50}$ = 15 µm |
| H2N-C(O)-CH2-X1 | H3C-(CH2)4-N(-(CH2)4-CH3)-C(O)-CH2-X2 | X3-N(-)-C(O)-O-CH2-fluorenyl | IIID IVA |
| (2,4,6-trimethoxybenzyl)-N-CH2-X1 | X2-CH2-C(O)-O-CH2-CH=CH2 | X3-N(-)-C(O)-O-CH2-fluorenyl | IVA $IC_{50}$ = 4 µM |
| (2,4,6-trimethoxybenzyl)-N-CH2-X1 | X2-CH2-C(O)-O-CH3 | X3-N(-)-C(O)-quinolin-3-yl | IIA $IC_{50}$ = 25 µM IIIA |

TABLE D-continued

| R¹ | R² | R³ | Biological Activity |
|---|---|---|---|
| 2,4,6-trimethoxybenzyl-N-CH₂-C(O)-X₁ | methyl ester CH₂-X₂-C(O)-OCH₃ | N-acetyl prolinamide with X₃ | IIIE |
| 2,4,6-trimethoxybenzyl-N-CH₂-C(O)-X₁ | allyl ester X₂-CH₂-C(O)-O-CH₂-CH=CH₂ | NH₂-X₃ | IIIE |
| 2,4,6-trimethoxybenzyl-N-CH₂-C(O)-X₁ | X₂-CH₂-COOH | quinoline-3-carboxamide with X₃ | IIIE |
| H₂N-C(O)-CH₂-X₁ | X₂-CH₂-COOH | quinoline-3-carboxamide with X₃ | IIIE |
| H₂N-C(O)-CH₂-X₁ | allyl ester X₂-CH₂-C(O)-O-CH₂-CH=CH₂ | quinoline-3-carboxamide with X₃ | IIIB, IVB |
| H₂N-C(O)-CH₂-X₁ | allyl ester X₂-CH₂-C(O)-O-CH₂-CH=CH₂ | Fmoc-NH-X₃ | IIIE |
| 2,4,6-trimethoxybenzyl-N-CH₂-C(O)-X₁ | allyl ester X₂-CH₂-C(O)-O-CH₂-CH=CH₂ | quinoline-3-carboxamide with X₃ | IIIA |

TABLE D-continued
| R¹ | R² | R³ | Biological Activity |
|---|---|---|---|
| 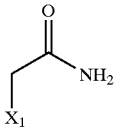 | 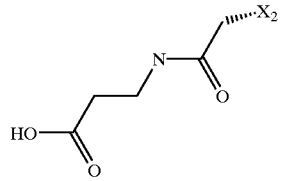 | 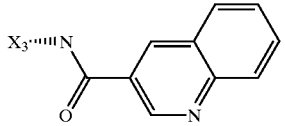 | IIIE |
| 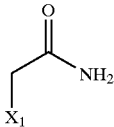 | 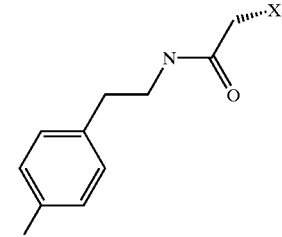 | 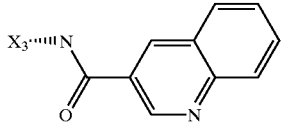 | IIIE |
| 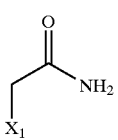 | 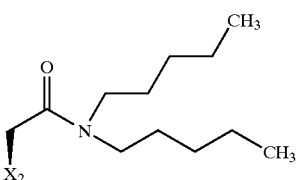 | 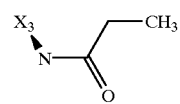 | IIE |
| 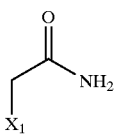 | 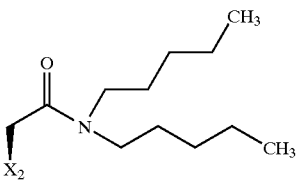 | 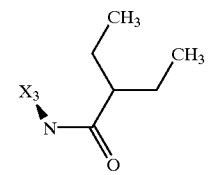 | IIC<br>IVD |
| 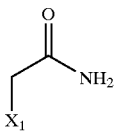 | 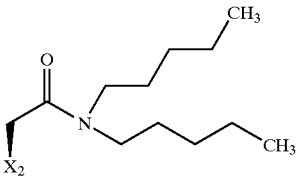 | 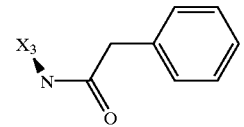 | IE<br>IIC<br>IVC |
| 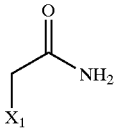 | 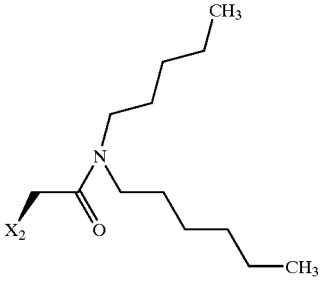 | 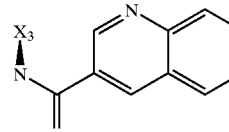 | IE<br>IID<br>IIIA<br>IC$_{50}$ = 8 μM<br>IVA<br>IC$_{50}$ = 30 μM |
| 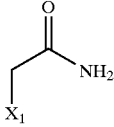 | 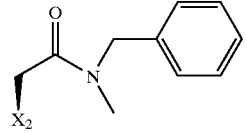 | 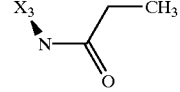 | IID |

TABLE D-continued
| R¹ | R² | R³ | Biological Activity |
|---|---|---|---|
| 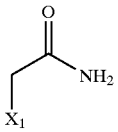 | 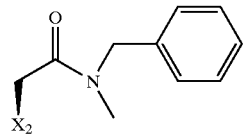 | 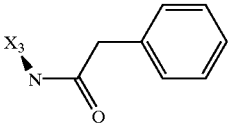 | IIE IVE |
| 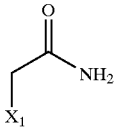 | 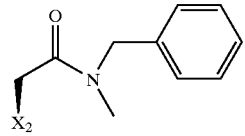 | 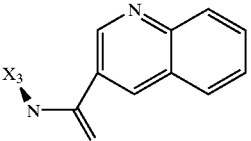 | IE IIC IVD |
| 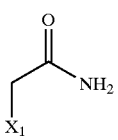 | 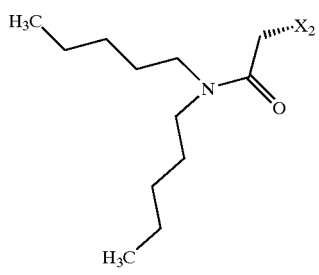 | 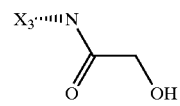 | IIE |
| 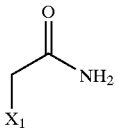 | 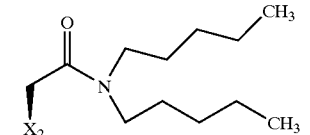 | 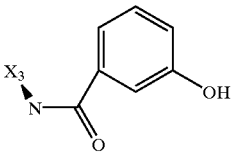 | IE IIE IVD |
| 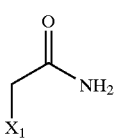 | 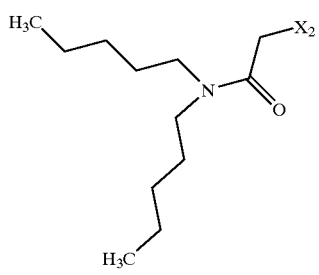 | 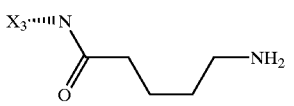 | IID |
| 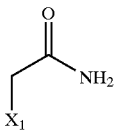 | 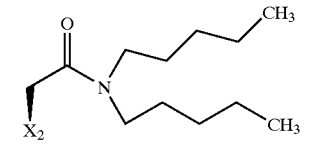 | 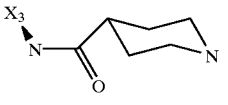 | ID IIE |
| 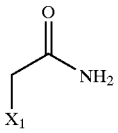 | 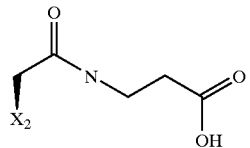 | 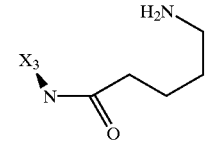 | IIE |
| 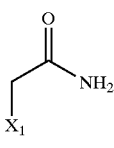 | 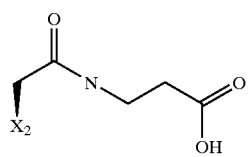 | 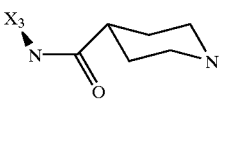 | IE |

TABLE D-continued

| R¹ | R² | R³ | Biological Activity |
|---|---|---|---|
| acetamide-X₁ | N,N-dipentyl acetamide-X₂ | X₃-NH-C(O)-CH₂CH₂-C(O)OH (glutaryl) | IE, IIE |
| acetamide-X₁ | N,N-dipentyl acetamide-X₂ | X₃-NH-C(O)-CH₂CH₂-C(O)N(CH₃)₂ | IE, IIE |
| acetamide-X₁ | N,N-dipentyl acetamide-X₂ | X₃-NH-C(O)-(N-acetyl prolinyl) | ID, IIE |
| acetamide-X₁ | N,N-dipentyl acetamide-X₂ | X₃-NH-C(O)-(5-oxoprolinyl) | IC, IID |
| acetamide-X₁ | N-(4-aminobutyl) acetamide-X₂ | X₃-NH-C(O)-CH₂CH₂-C(O)OH | IE, IIE |
| acetamide-X₁ | N-(4-aminobutyl) acetamide-X₂ | X₃-NH-C(O)-CH₂CH₂-C(O)N(CH₃)₂ | IE |
| acetamide-X₁ | N-(4-aminobutyl) acetamide-X₂ | X₃-NH-C(O)-(N-acetyl prolinyl) | IE, IIE |
| acetamide-X₁ | N-(4-aminobutyl) acetamide-X₂ | X₃-NH-C(O)-(5-oxoprolinyl) | IE, IID |
| acetamide-X₁ | N-(benzo[1,3]dioxol-5-ylmethyl) acetamide-X₂ | X₃-NH-C(O)-CH₂CH₂-C(O)OH | ID |
| acetamide-X₁ | N-(benzo[1,3]dioxol-5-ylmethyl) acetamide-X₂ | X₃-NH-C(O)-CH₂CH₂-C(O)N(CH₃)₂ | IE |

TABLE D-continued

| R¹ | R² | R³ | Biological Activity |
|---|---|---|---|
| (acetamide with X₁) | (piperonyl amide with X₂) | (pyroglutamate with X₃) | IE IID |
| (acetamide with X₁) | (N-acetylethylenediamine amide with X₂) | (glutaric acid derivative with X₃) | IID |
| (acetamide with X₁) | (N-acetylethylenediamine amide with X₂) | (N,N-dimethyl succinamide with X₃) | IE IID |
| (acetamide with X₁) | (N-acetylethylenediamine amide with X₂) | (N-acetyl proline amide with X₃) | IID |
| (acetamide with X₁) | (N-acetylethylenediamine amide with X₂) | (pyroglutamate with X₃) | ID IID |
| (acetamide with X₁) | (N-acetylethylenediamine amide with X₂) | (glutaric acid derivative with X₃) | IF IIE |
| (acetamide with X₁) | (N-acetylethylenediamine amide with X₂) | (N,N-dimethyl succinamide with X₃) | IIE |
| (acetamide with X₁) | (N-acetylethylenediamine amide with X₂) | (N-acetyl proline amide with X₃) | IE IID |
| (acetamide with X₁) | (N-acetylethylenediamine amide with X₂) | (pyroglutamate with X₃) | IE IIE |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of the structure (I):

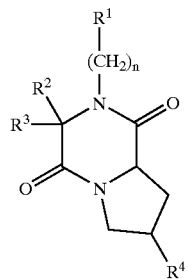

(I)

as an isolated isomer, diastereomer, or enantiomer, or a mixture thereof, or a pharmaceutically acceptable salt thereof; where, independently at each location:

$R^1$ is an aryl or a heteroaryl ring;

$R^2$ and $R^3$ are selected from hydrogen, alkyl, heteroalkyl, aryl, heteroaryl, carbocycle aliphatic ring, and heterocycle aliphatic ring;

n is 1, 2 or 3;

$R^4$ is —$NR^6R^7$; and $R^6$ and $R^7$ are independently selected from hydrogen, alkyl, heteroalkyl, aryl, heteroaryl, carbocycle aliphatic ring and heterocycle aliphatic ring or $R^6$ and $R^7$ taken together with the nitrogen atom to which they are attached form a heterocycle aliphatic ring.

2. The compound of claim 1 wherein $R^1$ is phenyl and the phenyl is substituted with 1–4 substituents independently selected at each occurrence from alkyl, heteroalkyl, aryl, heteroaryl, carbocycle aliphatic ring, and heterocycle aliphatic ring.

3. The compound of claim 2 wherein $R^1$ is phenyl having a substituent at the position para to the site of attachment to the piperazine ring.

4. A compound of the structure (I):

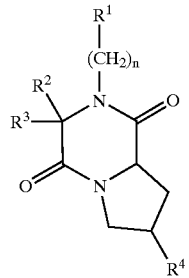

(I)

as an isolated isomer, diastereomer, or enantiomer, or a mixture thereof, or a pharmaceutically acceptable salt thereof; where, independently at each location:

$R^1$ is phenyl having a substituent at the position para to the site of attachment to the piperazine ring, and the substituent has the formula $R^{10}$—$R^9$—$R^8$—, wherein $R^8$ is selected from direct bond, alkylene and haloalkylene; $R^9$ is selected from direct bond and carbonyl; and $R^{10}$ is selected from hydrogen, $R^{11}$ —O—, $(R^{11})_2N$— and $R^{11}$ —(C=O)—NH—; wherein $R^{11}$ is selected from hydrogen and organic groups having 1–20 carbons and optionally containing 1–4 heteroatoms selected from oxygen and nitrogen;

$R^2$ and $R^3$ are selected from hydrogen, alkyl, heteroalkyl, aryl, heteroaryl, carbocycle aliphatic ring and heterocycle aliphatic ring;

n is 1, 2 or 3;

$R^4$ is —$NR^6R^7$; and $R^6$ and $R^7$ are independently selected from hydrogen, alkyl, heteroalkyl, aryl, heteroaryl, carbocycle aliphatic ring and heterocycle aliphatic ring or $R^6$ and $R^7$ taken together with the nitrogen atom to which they are attached form a heterocycle aliphatic ring.

5. The compound of claim 4 wherein $R^8$ is methylene; $R^9$ is carbonyl, and $R^{10}$ is $(R^{11})_2N$— wherein $R^{11}$ is selected from hydrogen and organic groups having 1–20 carbons and optionally containing 1–4 heteroatoms selected from oxygen and nitrogen.

6. The compound of claim 3 wherein $R^1$ is phenyl having a substituent at the position para to the site of attachment to the piperazine ring, and the substituent has the formula,

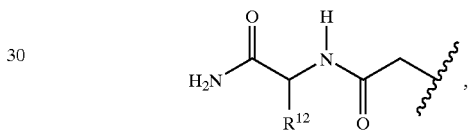

wherein $R^{12}$ is selected from hydrogen and organic groups having 1–20 carbons and optionally containing 1–4 heteroatoms selected from oxygen and nitrogen.

7. A The compound of claim 6 wherein $R^{12}$ is selected from hydrogen, alkyl, heteroalkyl, aryl, heteroaryl, carbocycle aliphatic ring and heterocycle aliphatic ring.

8. The compound of claim 6 wherein $R^{12}$ is selected from

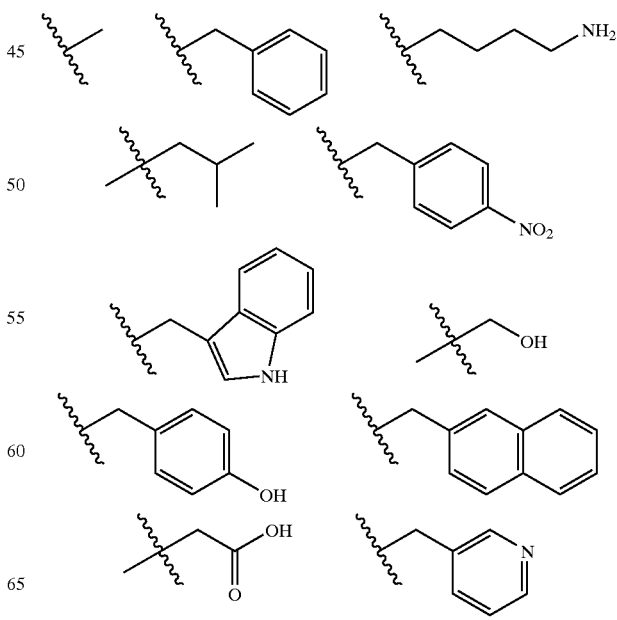

-continued

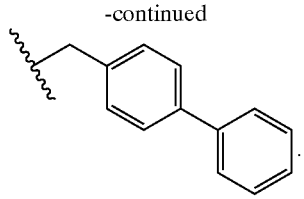

9. The compound of claim 1 wherein $R^1$ is phenyl.
10. The compound of claim 1 wherein n is 1.
11. A compound of the structure (I):

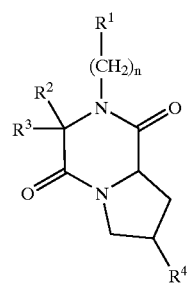

(I)

as an isolated isomer, diastereomer, or enantiomer, or a mixture thereof, or a pharmaceutically acceptable salt thereof; where, independently at each location:

$R^1$ is an aryl or a heteroaryl ring;

$R^2$ and $R^3$ are independently selected from groups of the formula $R^{10}$—$R^9$—$R^8$—, wherein $R^8$ is selected from direct bond, alkylene and haloalkylene; $R^9$ is selected from direct bond and carbonyl; and $R^{10}$ is selected from hydrogen, $R^{11}$—O—, $(R^{11})_2$N— and $R^{11}$—(C=O)—NH—; wherein $R^{11}$ is selected from hydrogen and organic groups having 1–20 carbons and optionally containing 1–4 heteroatoms selected from oxygen and nitrogen, with the proviso that two $R^{11}$ groups bonded to the same nitrogen may be bonded together so as to form a heterocyclic ring with the common nitrogen;

n is 1, 2 or 3;

$R^4$ is —$NR^6R^7$; and $R^6$ and $R^7$ are independently selected from hydrogen, alkyl, heteroalkyl, aryl, heteroaryl, carbocycle aliphatic ring and heterocycle aliphatic ring or $R^6$ and $R^7$ taken together with the nitrogen atom to which they are attached form a heterocycle aliphatic ring.

12. The compound of claim 11 wherein $R^8$ is methylene; $R^9$ is selected carbonyl, and $R^{10}$ is $(R^{11})_2$N—.

13. The compound of claim 12 wherein $R^{10}$ is selected from:

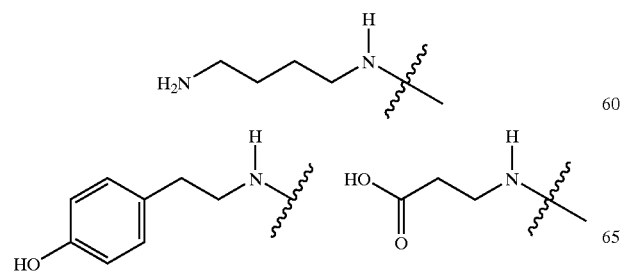

-continued

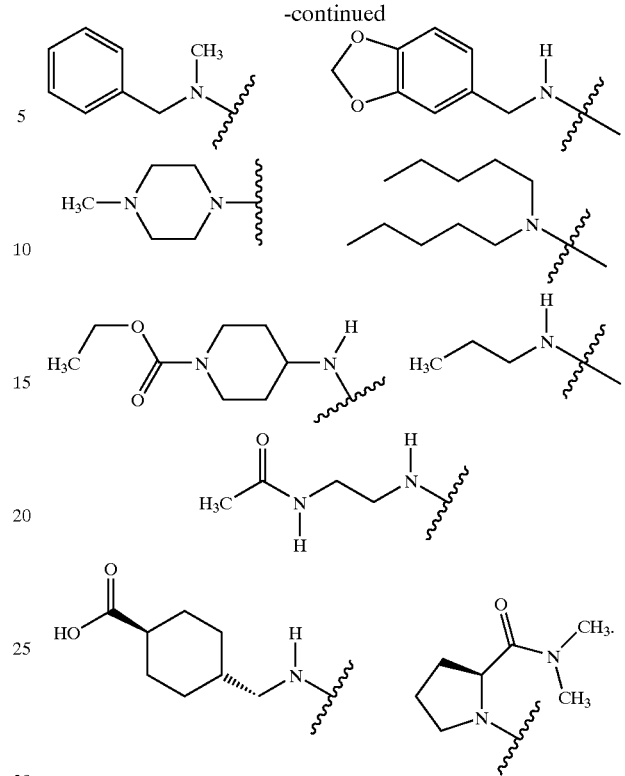

14. A compound of the structure (I):

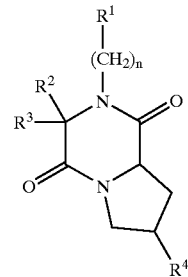

(I)

as an isolated isomer, diastereomer, or enantiomer, or a mixture thereof, or a pharmaceutically acceptable salt thereof; where, independently at each location:

$R^1$ is an aryl or a heteroaryl ring;

$R^2$ and $R^3$ are selected from hydrogen, alkyl, heteroalkyl, aryl, heteroaryl, carbocycle aliphatic ring, and heterocycle aliphatic ring;

n is 1, 2 or 3;

$R^4$ is —$NR^6R^7$; and $R^6$ hydrogen and $R^7$ is $R^{13}$ —C(=O)— where $R^{13}$ is selected from:

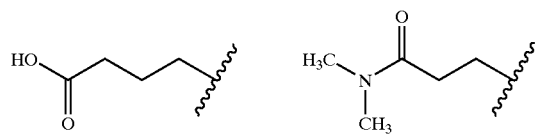

-continued

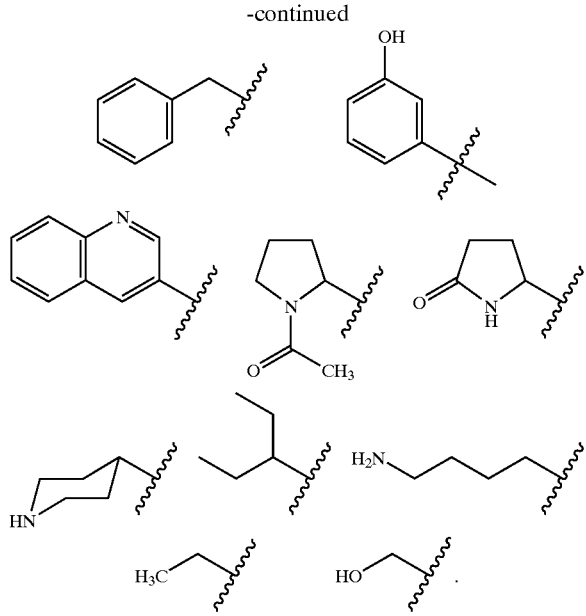

15. A pharmaceutical composition comprising a compound according to claim 1, 4, 11 or 14 and a pharmaceutically acceptable adjuvant, carrier, diluent or excipient.

16. A method of treating inflammation comprising administering to a subject in need thereof a therapeutically effective amount of a compound according to claim 1, 4, 11 or 14.

17. A method for inhibiting a TNF-α mediated processes, comprising administering to a patient in need thereof, through a therapeutically or prophylactically acceptable manner, a therapeutically or pharmaceutically effective amount of a composition comprising a compound of claim 1, 4, 11 or 14.

18. A method for inhibiting a TNF-α mediated processes, comprising administering to a patient in need thereof, through a therapeutically or prophylactically acceptable manner, a therapeutically or pharmaceutically effective amount of a composition comprising a compound of claim 1, 4, 11 or 14, wherein the administering is selected from transdermal, oral, intravenous, intramuscular, vaginal, rectal, pulmonary, subcutaneous, sublingual and transmucosal administration.

19. A method for inhibiting a TNF-α mediated processes, comprising administering to a patient in need thereof, through a therapeutically or prophylactically acceptable manner, a therapeutically or pharmaceutically effective amount of a composition comprising a compound of claim 1, 4, 11 or 14.

20. A method for treating a condition associated with an elevated level of NFκB activity in a subject, comprising administering to a subject in need thereof an amount of a compound effective to lower the NFκB activity, wherein the compound is a compound of claim 1, 4, 11 or 14.

21. A method of inhibiting IL-8 production in a subject in need thereof comprising administering to the subject an effective amount of a compound of claim 1, 4, 11 or 14.

22. A method of inhibiting GRO-α production in a subject in need thereof comprising administering to the subject an effective amount of a compound of claim 1, 4, 11 or 14.

23. A method for inhibiting a CXCR1 and/or CXCR2 mediated processes, comprising administering to a patient in need thereof, through a therapeutically or prophylactically acceptable manner, a therapeutically or pharmaceutically effective amount of a composition comprising a compound of claim 1, 4, 11 or 14.

24. The method of claim 23 wherein the method inhibits a CXCR1 mediated processes.

25. The method of claim 23 wherein the method inhibits a CXCR2 mediated processes.

26. The method according to claim 23 wherein the administering is selected from transdermal, oral, intravenous, intramuscular, vaginal, rectal, pulmonary, subcutaneous, sublingual and transmucosal administration.

27. A method for treating an inflammation event, comprising administering to a patient in need thereof, through a therapeutically or prophylactically acceptable manner, a therapeutically or pharmaceutically effective amount of a composition comprising a compound of claim 1, 4, 11 or 14.

28. The method according to claim 27 wherein the administering is selected from transdermal, oral, intravenous, intramuscular, vaginal, rectal, pulmonary, subcutaneous, sublingual and transmucosal administration.

29. A method for identifying binding partner to one or more compounds of claim 1, 4, 11, or 14, wherein the method comprises:
   immobilizing proteins known to be involved in the TNF-α signaling pathway onto a suitable carrier; and
   passing a solution of said compound(s) in isolation or mixture over said proteins and analyzing for compound:protein complex formation using surface plasmon resonance (SPR).

30. A method for identifying a binding partner to one or more compounds of claim 1, 4, 11 or, 14, wherein the method comprises:
   providing said compound(s) bound to a solid support to provide solid phase compound(s);
   contacting a cell or cell components containing said binding partner with said solid phase compound(s) in isolation or mixture to form a binding partner:solid phase compound(s) complex;
   removing uncomplexed cell or cell component material from binding partner:solid phase compound(s) complex; and
   recovering said binding partner from binding partner-solid phase compound(s) complex.

* * * * *